United States Patent [19]

Isowa et al.

[11] 4,436,925
[45] * Mar. 13, 1984

[54] ADDITION COMPOUND OF DIPEPTIDE DERIVATIVE AND AMINO ACID DERIVATIVE

[75] Inventors: Yoshikazu Isowa; Muncki Ohmori, both of Tokyo; Kaoru Mori; Tetsuya Ichikawa, both of Sagamihara; Yuji Nonaka, Shin-Nanyo; Keiichi Kihara, Shin-Nanyo; Kiyotaka Oyama, Shin-Nanyo; Heijiro Satoh, Shin-Nanyo; Shigeaki Nishimura, Shin-Nanyo, all of Japan

[73] Assignees: Toyo Soda Manufacturing Co., Ltd., Shin-Nanyo; Sajami Chemical Research Center, Tokyo, both of Japan

[*] Notice: The portion of the term of this patent subsequent to Mar. 17, 1998 has been disclaimed.

[21] Appl. No.: 270,025

[22] Filed: Jun. 3, 1980

Related U.S. Application Data

[60] Continuation of Ser. No. 119,654, Feb. 8, 1980, abandoned, which is a division of Ser. No. 20,058, Mar. 13, 1979, abandoned, which is a division of Ser. No. 870,108, Jan. 17, 1978, abandoned.

[30] Foreign Application Priority Data

Jan. 27, 1977 [JP] Japan .................................. 52-7279
May 19, 1977 [JP] Japan ................................ 52-57036

[51] Int. Cl.³ .......................................... C07C 101/00
[52] U.S. Cl. ................................................: 560/19
[58] Field of Search .................... 260/112.5 R; 560/19

[56] References Cited

U.S. PATENT DOCUMENTS 4,165,311  8/1979  Isowa et al. ................. 260/112.5 R
4,256,836  3/1981  Isowa et al. ........................... 435/70

FOREIGN PATENT DOCUMENTS 2801238  3/1978  Fed. Rep. of Germany ... 260/112.5 R
 508590  7/1971  Switzerland .
1243169  8/1971  United Kingdom .

OTHER PUBLICATIONS

Eliel, "Stereochemistry of Carbon Compounds" 1962, p. 49.

Primary Examiner—Delbert R. Phillips
Attorney, Agent, or Firm—Oblon, Fisher, Spivak, McClelland & Maier

[57] ABSTRACT

Addition compounds have the formula

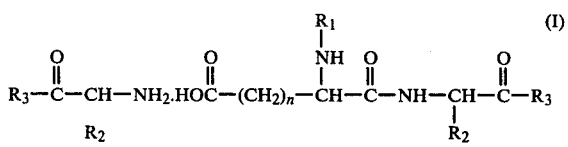

wherein $R_1$ represents an aliphatic oxycarbonyl group, benzyloxycarbonyl group which can have nuclear substituents or benzoyl, aromatic sulfonyl or aromatic sulfinyl group; $R_2$ represents methyl, isopropyl, isobutyl, isoamyl or benzyl group; $R_3$ represents a lower alkoxyl, benzyloxy or benzhydryloxy group and n represents 1 or 2.

The addition compounds are produced by reacting an N-substituted monoaminodicarboxylic acid having the formula

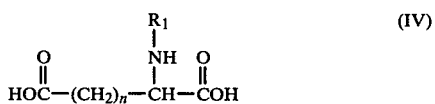

with an amino carboxlic acid ester having the formula

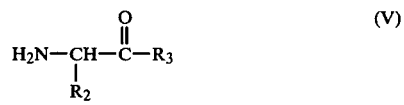

in an aqueous medium in the presence of a protease and reacting the resulting dipeptide ester with the amino carboxylic acid ester and separating the addition compound.

The addition compounds can be decomposed into the constituent dipeptide esters and amino acid esters by the action of an acid.

9 Claims, No Drawings

ADDITION COMPOUND OF DIPEPTIDE DERIVATIVE AND AMINO ACID DERIVATIVE

This is a continuation of application Ser. No. 119,654, filed Feb. 8, 1980, which is a division of application Ser. No. 020,058, filed Mar. 13, 1979, which in turn is a division of Ser. No. 870,108, filed Jan. 17, 1978, all now abandoned.

BACKGROUND OF THE INVENTION

1. Field of the Invention

The present invention relates to novel addition compounds of dipeptide derivative and amino acid derivative and a process for producing the addition compound. More particularly it relates to novel addition compounds of the dipeptides composed of N-substituted monoamino dicarboxylic acid ester residues and amino carboxylic acid ester residues, with amino carboxylic acid esters and processes for producing the addition compound utilizing an enzymatic reaction and for decomposing the addition compound.

2. Description of the Prior Art:

It has been known that protease such as papain and chymotrypsin are used for forming peptide bonds as the reverse reaction of protein decomposition. For example, anilides have been produced by using papain by Bergman and the peptide syntheses using monoamino monocarboxylic acids such as leucine having an N-terminal protective benzoyl group and leucine and glycine both having a C-terminal protective amide or anilide group have been attained with papain and chymotrypsin by Fruton. (Advances in Protein Chemistry Vol. 5, page 33 (1949). Academic Press Inc. New York, N.Y.)

Recently, some of the inventors reported peptide syntheses using amino acids having an N-terminal protective benzyloxycarbonyl group and amino acids having a C-terminal ester group with enzymes such as papain, Prolisin, subtilisin BPN', etc. (Abstracts of the 35th Autumun Conference of the Chemical Society of Japan, PP482 and 486 (1976).

In these processes, the products are deposited in an aqueous medium as water insoluble products resulted by losing water soluble groups (this is necessary to force the reversible reaction toward the peptide formation). Accordingly, when a water soluble group should still be remained in the reaction product, for example, as in the case wherein the aminoacids having a second carboxyl group at the side chain (e.g., aspartic acid and glutamic acid) are used as the starting compound, it has been assumed to be desirable that the water soluble group of the starting compound be masked with a less hydrophilic protective group.

The inventors have studied further on these systems and have found that, when monoaminodicarboxylic acids such as aspartic acid and glutamic acid which has an N-terminal protective group are used as the starting compounds, the resulting dipeptides themselves are not deposited, however, and that, when specific amino acids having a C-terminal ester group (amino carboxylic acid esters) are chosen for the counter part starting compounds, addition compounds of the dipeptides which are enzymatic reaction products, and the amino acid esters are deposited.

It has been known that peptide derivatives have various physiological activities, and these peptide derivatives can be produced by various methods. The peptides having acidic amino acid residue such as α-L-aspartyl-phenylalanine lower alkyl ester useful as a sweetening compound can be obtained from a precursor having a benzyloxycarbonyl group as an N-terminal protective group by removing the protective group.

The peptides having an N-terminal protective group such as N-benzyloxycarbonyl-L-α-glutamyl phenylalanine lower alkyl ester can be easily hydrolyzed to lead peptides having a bare C-terminal carboxyl group, and these hydrolyzed peptides have been used as substrates for measuring enzymatic activity of a carboxypeptidase.

The N-protected or -unprotected dipeptide esters can be obtained by reacting acidic amino acid anhydride having an amino group protected or unprotected with an amino acid alkyl ester (Japanese Patent Publication No. 14217/1974 and Japanese Unexamined Patent Publication Nos. 61451/1973, 76835/1973, 58025/1975 and 71642/1975). However, the desired dipeptide esters can not be obtained easily by the conventional processes, since according to these processes, dipeptide esters having peptide bonds at the side chain carboxyl groups of the acidic amino acids are inevitably produced with the desired ones.

SUMMARY OF THE INVENTION

The present invention is to provide addition compounds having the formula

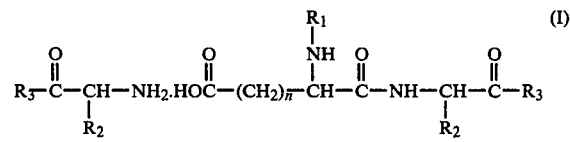

wherein $R_1$ represents an aliphatic oxycarbonyl group, benzyloxycarbonyl group which can have nuclear substituents, or benzoyl, aromatic sulfonyl or aromatic sulfinyl group, $R_2$ represents methyl, isopropyl, isobutyl, isoamyl or benzyl group; $R_3$ represents a lower alkoxyl, benzyloxy, benzhydryloxy group and n represents 1 or 2.

The addition compounds having formula (I) include fragmentary units of the formula

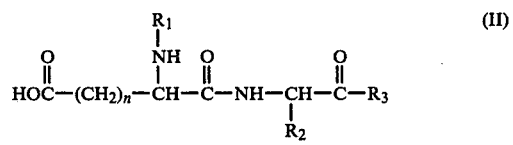

which may be in LL-form and also of the formula

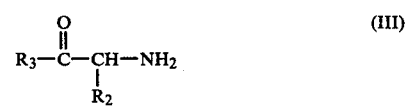

which may be in L-, D- or mainly D-form, wherein $R_1$, $R_2$ and $R_3$ in the formulae (II) and (III) have the same meaning as in formula (I).

This invention is also to provide a process for producing the addition compounds. The addition compounds are produced by reacting an N-substituted monoaminodicarboxylic acid having the formula

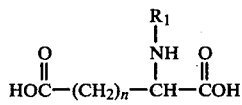

with an amino carboxylic acid ester having the formula

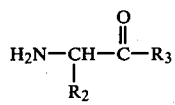

wherein $R_1$, $R_2$ and $R_3$ have the same meanings as in formula (I), in an aqueous medium in the presence of a protease and reacting the resulting dipeptide ester with the amino carboxylic acid and separating the addition compound. The N-substituted monoaminodicarboxylic acid having the formula (IV) and the amino acid esters having formula (V) are in L-form or DL-form.

This invention is to further provide a process for conducting an optical resolution of the N-substituted monoaminodicarboxylic acid having formula (IV) and the amino acid ester having formula (V).

This invention is to still further provide a process for decomposing the addition compounds. The addition compounds are treated with an acidic solution for separating the solid component to obtain the corresponding dipeptide esters having the formula

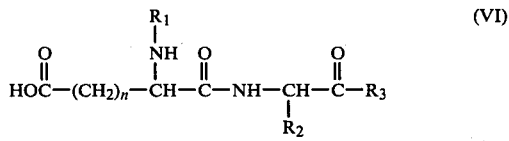

wherein $R_1$, $R_2$ and $R_3$ have the same meanings as in formula (I).

The addition compounds wherein $R_1$ is N-p-methoxybenzyloxycarbonyl are dissolved in a liquid medium and treated with an acid to produce dipeptide esters having a bare amino group of the formula

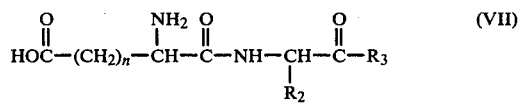

wherein $R_2$ and $R_3$ have the same meanings as in formula (I).

The present invention is to produce α-L-aspartyl-L-phenylalanine alkyl esters which have sweet taste as sugar α-L-Aspartyl-L-phenylalanine methyl ester has a sweetness of about 200 times of that of sugar in one of it's specific objects.

DETAILED DESCRIPTION OF THE PREFERRED EMBODIMENTS

In the formula (I) of the addition compounds of the present invention, the aspartic acid skeleton is given in the case of n−1 and the glutamic acid skeleton is given in the case of n=2.

In the formula (I) of the addition compounds of the present invention, $R_1$ includes aliphatic oxycarbonyl groups such as t-butyloxycarbonyl group ($(CH_3)_3C-O-CO-$) and t-amyloxycarbonyl group ($(CH_3)_2C(C_2H_5)-O-CO-$) and benzyloxycarbonyl group ($\phi-CH_2-O-CO-$) and nuclear substituted benzyloxycarbonyl groups such as p-methoxybenzyloxycarbonyl group ($p-CH_3O-\phi-CH_2-O-CO-$), 3,5-dimethoxybenzyloxycarbonyl group ($(3,5-(CH_3O)_2-\phi-CH_2-O-CO-$), 2,4,6-trimethoxybenzyloxycarbonyl group ($(2,4,6-(CH_3O)_3-\phi-CH_2-O-CO-$); benzoyl group ($\phi-CO-$); p-toluenesulfonyl group ($p-CH_3-\phi-SO_2-$); and aromatic sulfinyl groups such as o-nitrosulfinyl group.

In the formula (I), alanine skeleton is given in the case of $R_2$=methyl group; valine skeleton is given in the case of $R_2$=isopropyl group; leucine skeleton is given in the case of $R_2$=isobutyl group and isoleucine skeleton is given in the case of $R_2$=isoamyl group and phenylalanine skeleton is given in the case of $R_2$=benzyl group.

In the formula, $R_3$ is alcohol residue such as lower alkoxy groups such as methoxy group ($CH_3O-$); ethoxy group ($C_2H_5O-$); propoxy group ($C_3H_7O-$); butoxy group ($C_4H_9O-$), and benzyloxy group and benzhydryloxy group.

Typical examples of $R_1$, $R_2$ and $R_3$ are as follows:

$R_1$; benzyloxycarbonyl and p-methoxybenzyloxycarbonyl:

$R_2$; benzyl:

$R_3$; methoxy and ethoxy.

The addition compounds of the present invention show characteristics reasonably expected from the formula (I). For example, a typical addition compound obtained by the reaction of N-benzyloxycarbonyl-L-aspartic acid and L-phenylalanine methyl ester, shows the absorptions in the infrared and NMR spectra as follows.

Infrared spectrum $3,260^{cm-1}$ (N—H stretching vibration); 3,000 to $3,200^{cm-1}$ (C—H stretching vibration); $1,740^{cm-1}$ (C=O ester); $1,720^{cm-1}$ (C=O urethane); $1,660^{cm-1}$ (amide 1st absorption); $1,630^{cm-1}$ (carboxylate); $1,540^{cm-1}$ (amide 2nd absorption); 1,430 and $1,450^{cm-1}$ (C—H deformation vibration); $1,390^{cm-1}$ (carboxylate); 1,220 to $1,290^{cm-1}$ (C—O—C stretching vibration and amide 3rd absorption); $1,050^{cm-1}$ (phenyl in-plane vibration); and 740 and $695^{cm-1}$ (monosubstituted benzene ring out-of-plane vibration).

NMR spectrum (1) δ=2.75 ppm (2H)
(2) δ=3.02 ppm (4H)
(3) δ=3.61 ppm (3H) 3.7 ppm (3H)
(4) δ=4.4 to 4.8 ppm (3H)
(5) δ=5.05 ppm (2H)
(6) δ=5.82 ppm (5H)
(7) δ=7.3 ppm (15H)

The data of the elementary analysis of the addition compound are substantially the same with the calculated values for the formula (I) wherein $R_1$, $R_2$ and $R_3$ are benzyl oxycarbonyl, benzyl and methyl, respectively, and n is 1.

When the addition compound is treated with a strong acid such as hydrochloric acid and the product is extracted with an organic solvent such as ethyl acetate, an acidic compound is obtained from the organic layer. When the above-mentioned typical addition compound is so treated, the resulting acidic compound shows characteristics and properties expected as the compound shown in formula (VI) in LL-form wherein $R_1$, $R_2$, $R_3$ and n are same as in the above-mentioned typical addition compound.

When the acidic compound prepared from the above-mentioned typical addition compound is catalytically reduced with hydrogen, the product is known LL-aspartyl-phenylalanine methyl ester.

All the data including infrared and NMR spectra and elementary analyses of the compounds obtained at any of the above stages support the structures shown in the formulae.

The identically corresponding results are also obtained in the case wherein the compounds with other $R_1$, $R_2$, $R_3$ and n are chosen.

When the addition compounds of the present invention are treated in an aqueous medium with a strong acid such as hydrochloric acid and the product is extracted with an organic solvent, the compounds having the formula (VI) can be obtained. On the other hand, L-form, D-form or mainly D-form amino carboxylic acid ester having formula (III) can be recovered from the aqueous phase, whereby the optical isomerism of the recovered esters is dependent upon that of the fragmentary units shown in formula (III) of the addition compounds.

In this case, the amount of the compound having the formula (VI) is equivalent to the resulting amino carboxylic acid ester having formula (III) whereby it is clear that the original compound is the addition compound of dipeptide ester and amino carboxylic acid ester (1:1) which has the formula (I).

The addition compounds of the present invention may have water for crystallization. The addition compounds of the present invention are remarkably useful intermediates in the peptide syntheses.

As stated above, when the addition compound of the present invention is treated with a strong such as hydrochloric acid and then the product is extracted with an organic solvent, the dipeptide having a protective group for the amino group can be obtained.

When the protective group for the amino group i.e. $R_1$ is removed by a known method such as a catalytic hydrogenation, the dipeptide ester having one amino group and one carboxyl group can be obtained.

The resulting dipeptide esters are remarkably useful compounds.

For example, α-L-aspartyl-phenylalanine lower alkyl esters, especially methyl ester wherein n is 1. $R_2$ is benzyl group and $R_3$ is lower alkoxy, especially methoxy group, can be used as sweetening material.

A peptide having an N-terminal protective group and a bare C-terminal carboxyl group, which can be derived from the dipeptide ester having a protective group for the amino group according to a conventional hydrolysis technique, is also useful. For example, N-benzyloxycarbonyl-α-L-glutamyl phenylalanine is used as a substrate for measuring the enzymatic activity of a carboxypeptidase as previously mentioned.

The present invention is also to produce the addition compounds by reacting an N-substituted monoaminodicarboxylic acid with an amino carboxylic acid ester in the presence of a protease and bonding the resulting dipeptide ester to the amino carboxylic acid ester and recovering the addition compound.

That is, one of the process of the present invention is to produce the addition compound of dipeptide ester and amino carboxylic acid ester having the formula (I) by reacting an N-substituted monoaminodicarboxylic acid having the formula (IV) with an amino acid ester having the formula (V) in an aqueous medium in the presence of a protease in a pH range wherein the protease exerts enzymatic activity and bonding the resulting dipeptide ester to the amino carboxylic acid ester and separating the addition compound.

The starting compounds of N-substituted monoaminodicarboxylic acids are N-substituted aspartic acid in the case of $n=1$ and N-substituted glutamic acid in the case of $n=2$.

$R_1$ is a protective group for amino group and it protects the amino group in the reaction of the present invention. It is necessary that $R_1$ is stable during the reaction. When $R_1$ is removed from the amino group after the reaction, it is necessary that $R_1$ can be removed without an effect to the skeleton of the product.

Since the product is separated from the aqueous medium by depositing t, it should not have a group preventing the deposition as sulfonic acid group which highly enhances the water solubility of the product.

The N-substituted monoaminodicarboxylic acids used in the present invention can be easily obtained by introducing the protective group of $R_1$ to the monoaminodicarboxylic acid by the convention processes.

The amino carboxylic acid esters used as the other starting compounds are amino acid esters having a hydrophobic group at the side chain and they are alanine esters in the case of $R_2$=methyl group; valine esters in the case of $R_2$=isopropyl group; leucine esters in the case of $R_2$=isobutyl group; isoleucine esters in the case of $R_2$=isoamyl group and phenylalanine esters in the case of $R_2$=benzyl group. Of these $R_2$ groups, the benzyl group which gives phenylalanine esters as the amino acid ester is the most typical case.

The proteases used in the present invention are preferably metalloproteases which have a metal ion in the active centre. Suitable metalloproteases are enzymes originating from microorganisms, such as neutral proteases from ray fungus, Prolisin, Thermolycin, Collagenase, Crotulus atrox protease, etc. It is also possible to use crude enzymes such as Thermoase, Tacynase-N.Pronase etc. In order to inhibit the action of esterase contained in the crude enzymes, it is preferable to use an enzyme inhibitor such as a potato inhibitor with the crude enzymes. It is possible to use thiol proteases such as parain or serine proteases such as trypsin, however they have esterase activity. Therefore, precaution must be paid when conducting the reaction using such an enzyme for preventing the hydrolysis of esters.

In the syntheses of the present invention, the peptide linkage formation reaction is performed in an aqueous medium, preferably aqueous solutions, under the pH condition wherein the protease exerts the enzymic activity.

The reaction for forming the addition compound of peptide and amino carboxylic acid ester is also pH dependent. It is preferable to perform the reactions of the present invention in a pH range of about 4 to 9 especially about 5 to 8. Accordingly, the starting compounds of the N-substituted monoaminodicarboxylic acids and the amino carboxylic acid esters can be in a free form or a salt form, however, when both of them are dissolved in the aqueous medium, it is necessary to adjust pH in said range.

Suitable pH adjusting agents include inorganic or organic acids and bases such as hydrochloric acid, sulfuric acid, and acetic acid; alkali metal hydroxides such as sodium hydroxide and potassium hydroxide; alkali metal carbonates such as sodium carbonate, sodium bicarbonate, potassium carbonate, and potassium bicarbonate; and organic and inorganic amines such as ammonia, trimethylamine, triethyl amine, ethanol amine etc.

The amounts of hydrogen ions and hydroxy ions liberated in the reaction are equivalent whereby the variation of pH by the reaction is not high. Thus, in order to prevent the variation of pH, it is possible to use a buffer agent. In the industrial process it is convenient to control pH by using a pH controlling device in response to a pH detecting device.

The aqueous medium is usually an aqueous solution. It is possible to add a water miscible organic solvent to the aqueous medium to the extent that the solvent does not prevent the deposition of the product.

The reaction of the present invention is carried out in a temperature range of about 10° to 90° C., preferably 20° to 50° C. from the viewpoint of maintaining enzymatic activity. The reaction is usually completed for about 30 minutes to 24 hours though it is not critical.

The concentrations of both of the starting compounds in the reaction medium are not critical. The process of the present invention is essentially depending upon the deposition of the product, whereby the concentrations are preferably higher. The solubilities of the product addition compounds in water are relatively low. For example, the solubility of the addition compound of N-benzyloxycarbonyl-L-aspartyl-L-phenylalanine methyl ester and L-phenylalanine methyl ester is about 0.3 g/100 g water at 20° C. Accordingly, the concentrations can be relatively low and usually in a range of about 0.001 M to 7 M preferably 0.1 M to 4 M.

The ratio of the used starting compounds is not critical. However, the reaction of the present invention is to bond one molecule of the N-substituted monoaminodicarboxylic acid to two molecules of the amino carboxylic acid ester whereby the stoichiometric molar ratio of the starting compounds is 1:2, and actually used ratio is usually in a range of 100:1 to 1:100 preferably 5:1 to 1:5 especially 2:1 to 1:3.

It is not always necessary to dissolve all the amounts of the starting compounds in the aqueous medium and it is possible to suspend partial amounts of the starting compounds since the concentrations of the starting compounds are decreased as the reaction proceeds whereby the suspended starting compounds are gradually dissolved.

In this case, the variation of pH may be caused whereby it may be necessary to adjust a pH of the solution as the reaction proceeds.

The amount of the protease used in the process of the present invention is not critical. When the concentration of the enzyme is high, the reaction can be completed in a short time. When the concentration of the enzyme is low, the reaction time is prolonged. Thus, it is usually in a range of about 2 to 400 mg ($5 \times 10^{-5}$ to $1 \times 10^{-2}$ mmol) per 1 mmol of the starting compounds, preferably about 5 to 100 mg ($1 \times 10^{-4}$ to $3 \times 10^{-3}$ mmol) per 1 mmol of the starting compounds.

The peptide linkage formation reaction of the present invention occurrs only on L-isomers but not on D-isomers. On the other hand, the amino acid esters used for conducting the addition reaction to form the addition compounds can be either L-form, D-form or a mixture thereof. When DL-form amino carboxylic acid ester is used, L-isomer of the DL-amino carboxylic acid ester in the solution is consumed in the peptide syntheses, whereby the remaining amino acid ester having predominant D-form is used for the production of the addition compound of dipeptide ester and amino carboxylic acid ester.

The reaction of the present invention performed in substantially quantitative yield when the concentrations of the starting compounds are high. When two moles of DL-form amino carboxylic acid esters is used per 1 mole of L-form N-substituted monoaminodicarboxylic acid, the addition compound substantially composed of LL-dipeptide ester and D-amino carboxylic acid ester can be obtained. Thus resulting addition compound can be easily divided into two frequentary components, that is, the LL-dipeptide ester and the D-amino acid ester as described above. Accordingly, the production of the dipeptide ester and the optical resolution of the DL-amino carboxylic acid ester can be simultaneously attained in this process.

The separated D-form or predominant D-form amino acid ester can be racemized according to a conventional method and the product can be used as the starting compound of the process of the present invention.

When a DL-form N-substituted monoaminodicarboxylic acid and the L-form acid ester are used, the D-isomer of the DL-form N-substituted monoaminodicarboxylic acid is inert to remain in the aqueous medium whereby the addition compound of LL-dipeptide ester and L-amino carboxylic acid ester can be obtained. Accordingly, when the D-form N-substituted monoaminodicarboxylic acid is recovered from the aqueous medium, it is possible to simultaneously attain the production of the addition compound and the optical resolution of the N-substituted-DL-monoaminodicarboxylic acid. When the recovered N-substituted-D-monoaminodicarboxylic acid is racemized according to a conventional method, the product can be used as the starting compound.

When the DL-form N-substituted monoaminodicarboxylic acid and the DL-form amino carboxylic acid ester are used, the N-substituted-DL-monoaminodicarboxylic acid can be obtained from the aqueous medium and the addition compound of LL-dipeptide ester and the D-amino carboxylic acid ester can be obtained, which addition compound can be divided to the components as mentioned-above. Then the production of the dipeptide ester and the optical resolutions of the N-substituted-DL-monoaminodicarboxylic acid and the DL-amino carboxylic acid ester can be simultaneously attained.

In accordance with the process of the present invention, it is possible to eliminate the steps of introducing and removing a protective group for the carboxyl group in a side chain which have been considered to be indispensable in the conventional processes. Accordingly, the loss of the starting compounds can be prevented. The yield of the products can be remarkably high when suitable conditions are selected.

In the process of the present invention, DL-form starting compounds can be used. In the usual processes using an enzyme, D-isomer of the DL-form starting compounds are useless in the reaction though not affecting the reaction and therefore it tends to cause the loss of the starting compounds. However, in the process of the present invention, the D-type starting compounds can be effectively used for the agent for depositing the dipeptide and they can be recovered afterward.

In the process of the present invention, the optical resolution of the N-substituted DL-aminodicarboxylic acid and the DL-amino carboxylic acid ester can be simultaneously attained.

This invention further provides processes for decomposing the addition compounds. The addition compounds having formula (I) are mixed with an aqueous acidic solution, and the peptide esters having formula (VI) are then recovered by separation as the remaining solid.

The acidic components of the aqueous acidic solution can be inorganic or organic acids. Suitable inorganic acids include hydrochloric acid, hydrobromic acid, sulfuric acid, phosphoric acid etc. Suitable organic acids include formic acid, acetic acid, citric acid, toluenesulfonic acid etc. The concentration of the acid is not critical and can be decided by the other conditions.

The acidic component in the acidic aqueous solution per the addition compound having the formula (I) is in the stoichiometric amount or more such as 1 to 100 eq. preferably 1 to 20 eq. especially 1 to 10 eq. per 1 mole of the addition compound (I) because the acidic component is used for ionizing the amino carboxylic acid ester unit to result in an aqueous solution of the salt thereof.

In some purposes, the dipeptide ester (VI) does not need to be highly pure. In such case, it is possible to use less amount of the acidic component than the stoichiometric relation such as 0.5 eq. per 1 mole of the addition compound (I). In some practical purposes, it can be, for example, about 0.8 eq. per 1 mole of the addition compound (I).

The ratio of the acidic aqueous solution to the starting compounds should be in a range wherein the dipeptide ester (VI) can exist in a solid state since the resulting dipeptide ester (VI) is separated as solid. However, the dipeptide esters (VI) have low solubility to water or the acidic aqueous solution, for example, in the case of N-benzyloxycarbonyl-L-aspartyl-L-phenylalanine methyl ester, of which solubility is 0.028 g/100 g water and 0.017 g/100 g diluted hydrochloric acid ($10^{-2}$ M) at 25° C. Accordingly, the ratio of the acidic aqueous solution can be relatively high. In the process of the present invention, on the other hand, the addition compound (I) is contacted with the acidic aqueous solution so as to be in the solid-liquid separable condition. Accordingly, it is not suitable to use too low ratio. Suitable amount of the acid aqueous solution is in a range of 1.5 to 50 wt. parts, preferably 2 to 10 wt. parts per 1 wt. part of the addition compound (I).

The temperature for reacting the addition compound (I) with the acidic aqueous solution is usually in a range of 0° to 100° C., preferably 5° to 80° C. When the stirring of the mixture is carried out enough, the decomposition of the addition compound (I) is completed in about 10 minutes.

When the protective group $R_1$ is one which may be easily hydrolyzed, such as p-methoxybenzyloxycarbonyl group, it is necessary to control the reaction time and the reaction temperature with precaution so as to prevent the removal of the group.

According to the process, the addition compound is decomposed to produce the dipeptide ester (VI) and a salt of the amino acid ester (V) with an acid component of the aqueous acid solution. A substantial part of the dipeptide ester (VI) is in the solid state after the decomposition reaction, since it has the low solubility in the aqueous acid solution as mentioned above. As the salt is well dissolved in the solution, the reaction system becomes a mixture of the solid dipeptide ester and the salt solution which may contain an excess of the acid component. The resulting solid dipeptide ester can be separated in a conventional way such as filtration or centrifugation. From the separated salt solution the amino acid ester can be recovered in a conventional way such as crystallizing out or solvent extraction after the liberation of the amino acid ester.

In accordance with the process, the dipeptide ester (VI) can be easily produced and separated by decomposing the addition compound (I) without complicated steps of an extraction and an ion exchange resin treatment. The yield and purity of the dipeptide ester (VI) can be remarkably high.

The production of α-L-aspartyl-L-phenylalanine alkyl esters used as sweetening materials will be further illustrated.

The other process of decomposition of the addition compound (VI) in a particular case is that the addition compound (VI) wherein $R_1$ is N-p-methoxybenzyloxycarbonyl, especially the addition compound of N-p-methoxybenzyloxycarbonyl-α-aspartyl-phenylalanine alkyl ester and phenylalanine alkyl ester (1:1) is dissolved in a liquid medium and decomposed with an acid in the liquid medium to obtain the dipeptide ester having a bare amino group of the formula (VII).

Suitable liquid media used for dissolving the addition compound (I) include organic solvents especially, ketones such as acetone; oxygen-containing organic solvents such as dioxane and tetrahydrofuran; chlorinated lower hydrocarbons such as chloroform, methylenedichloride, ethylenedichloride; non-protonic polar organic solvents such as dimethylformamide, dimethylsulfoxide and liquid carboxylic acids such as acetic acid and formic acid. A mixture of two or more solvents can be used.

It is possible to use esters such as ethyl acetate and alcohols such as methanol, ethanol and propanol. When these solvents are used, the yield of the product is usually lowered because of an undesirable side reaction such as the trans-esterification reaction or the esterification to the carboxyl group.

The addition compound has low solubility to water. Accordingly, water itself is not suitable as the liquid medium in this case though it is possible to add water to the liquid medium to the extent that enough solubility of the addition compound to the liquid medium is preserved.

The amount of the liquid medium is decided depending upon the kind of the liquid medium and the dissolution ability to the addition compound and it is usually higher than 10 wt. parts, preferably in a range of 20 to 100 wt. parts per 1 wt. part of the addition compound.

The acids used for decomposing the addition compound are Brønsted acid, preferably inorganic acids such as hydrochloric acid, hydrobromic acid, sulfuric acid, phosphoric acid, perchloric acid and organic acids such as trifluoro acetic acid, p-toluene sulfonic acid etc.

The ratio of the acid to the addition compound is preferably at least the stoichiometric relation and more particularly 2 equivalent or more of the acid per 1 mole of the addition compound.

The concentration of the acid in the liquid medium is usually in a range of 0.1 to 10 N, preferably 1 to 5 N and it is desirable to decide the actual concentration considering the other reaction conditions since the reaction may also be depending upon reaction time, the reaction temperature and the kind of the acid etc. However, high concentrations exceeding the above range which may cause undesirable side reactions such as hydrolysis of esters should be avoidable.

The acid can be aqueous or anhydrous ones. When the water inmiscible liquid medium such as chlorinated hydrocarbon is used it is preferable to use an anhydrous acid, since if an aqueous acid is used two phases are formed to give a very slow reaction.

The reaction temperature and time are not critical and the reaction is usually performed at 20° to 100° C. for 10 minutes to 6 hours.

When the acid is used in a lower concentration, the reaction time may be longer or the reaction temperature higher. When the concentration of the acid is higher, it is desirable to chose a shorter reaction time and a lower reaction temperature.

After decomposing the addition compound, the resulting dipeptide ester having the bare amino group (VII), anise alcohol and the amino acid ester (V) can be separated by the following methods. For example, after the reaction, anise alcohol is extracted in a solvent phase formed by adding a suitable amounts of water and a solvent capable of forming a separated phase with water such as chloroform and diethyl ether to the reaction solution followed by mixing and settling to result in two phases of the solvent and aqueous. On the other hand, pH of the aqueous phase is adjusted to 5 to 6 with a base such as NaOH, NaHCO$_3$, Na$_2$CO$_3$, ammonia, triethyl amine etc. and the deposited dipeptide ester having the bare amino group (VII) is separated by a filtration or the like. The pH of the filtrate is further adjusted to 8 to 10 with the base and the resulting free phenylalanine alkyl ester is extracted with a solvent such as chloroform, diethyl ether, ethyl acetate etc. The dipeptide ester having the bare amino group and amino acid ester can be also easily recovered with the conventional method using a cation-exchange resin.

The optical resolution techniques discussed above are also applied in this case.

This process is most effectively applicable to the production of α-L-aspartyl-phenylalanine lower alkyl ester from the addition compound of N-p-methoxybenzyloxycarbonyl-α-L-aspartyl-L-phenylalanine lower alkyl ester with phenylalanine lower alkyl ester, wherein R$_1$, R$_2$, R$_3$ and n are N-p-methoxybenzyloxycarbonyl, benzyl, lower alkyl, especially methyl or ethyl and 1, respectively.

According to the process, the removal of the aminocarboxylic acid fragmentary unit and the N-terminal protective group of p-methoxybenzyloxycarbonyl group from the dipeptide ester can be simultaneously attained. The separated anise alcohol can be recovered and converted to a p-methoxybenzyloxycarbonylation agent by reacting it with phosgene.

The present invention will be further illustrated by certain examples, which are included for purposes of illustration only.

EXAMPLE 1

A 1.335 mg (5 m mol) of N-benzyloxycarbonyl L-aspartic acid and 1,078 mg (5 m mol) of L-phenylalanine methyl ester hydrochloride were charged in a 30 ml flask and 20 ml of water was added to dissolve them and pH was adjusted to 6 with 7% ammonia water.

The resulting solution was admixed with 50 mg of Thermolysin and shaken at 38° to 40° C. over one night. The precipitate was collected and washed with 40 ml of water and dried to obtain 1,145 mg of fine needle like crystals having a melting point of 117° to 120° C. (an addition compound of N-benzyloxycarbonyl-L-aspartyl-L-phenylalanine methyl ester and L-phenylalanine methyl ester (1:1); (yield: 75.5% based on L-phenylalanine methyl ester hydrochloride).

The product was recrystallized from a solvent mixture of ethyl acetate and n-hexane. The physical properties and results of elementary analysis of the product were as follows.

Melting point: 120° to 124° C.
$[\alpha]_D^{25}$: +7.1 (C=1, methanol)

| Elementary analysis (C$_{32}$H$_{37}$N$_3$O$_9$) | | | |
|---|---|---|---|
| | C | H | N |
| Calculated (%) | 63.24 | 6.13 | 6.97 |
| Found (%) | 63.15 | 6.15 | 7.00 |

Infrared and NMR spectra of this product gave the same characteristics as described above.

A 1,145 mg of the resulting product was dissolved in 40 ml of 1 N-HCl and extracted with 30 ml of ethyl acetate 3 times. The extracts were mixed and washed with each 20 ml of water (3 times) and dehydrated with anhydrous magnesium sulfate. The solution was concentrated and the crystallization out was carried out by adding n-hexane to obtain 640 mg of a crystalline product. The physical properties and results elementary analysis of the product were as follows.

Melting point: 115° to 125° C.
$[\alpha]_D^{25}$: −15.3 (C=1, methanol)

| Elementary analysis (C$_{22}$H$_{24}$N$_2$O$_7$) | | | |
|---|---|---|---|
| | C | H | N |
| Calculated (%) | 61.67 | 5.65 | 6.54 |
| Found (%) | 61.52 | 5.65 | 6.57 |

Infrared and NMR spectra showed characteristics expected in N-benzyloxycarbonyl-L-aspartyl-L-phenylalanine methyl ester.

The results coincide with those of a compound obtained by a benzyloxycarbonylation of the amino group of L-aspartyl-L-phenylalanine methyl ester.

L-phenylalanine methyl ester was recovered from a mixture of the hydrochloric acid phase and the washing water fraction separated by the extraction from the ethyl acetate phase.

Accordingly, it was confirmed that the compound obtained by the former reaction was an addition compound of N-benzyloxycarbonyl L-aspartyl-L-phenylalanine methyl ester and L-phenylalanine methyl ester. It was also confirmed from NMR spectrum that their molar ratio was 1:1.

EXAMPLE 2

A 1,335 mg (5 m mol) of N-benzyloxycarbonyl-L-aspartic acid and 1,078 mg (5 m mol) of L-phenylalanine methyl ester hydrochloride were charged in a 30 ml flask and 10 ml of water was added to dissolve them and pH was adjusted to 6 with 7% ammonia water.

The resulting solution was admixed with 50 mg of Thermolysin and shaken at 38° to 40° C. over one night. The precipitate was collected and separated from the solution and dried to obtain 1,504 mg of an addition compound of N-benzyloxycarbonyl-L-aspartyl-phenylalanine methyl ester and L-phenylalanine methyl ester (1:1) (yield: 99.1% based on L-phenylalanine

EXAMPLE 3

In accordance with the process of Example 2 except varying the amounts of N-benzyloxycarbonyl-L-aspartic acid and L-phenylalanine methyl ester to 534 mg (2 m mol) and 863 mg (4 m mol) respectively, the reaction and the treatment were carried out to obtain 1,068 mg of an addition compound of N-benzyloxycarbonyl-L-aspartyl-L-phenylalanine methyl ester and L-phenylalanine methyl ester (1:1). (melting point: 116° to 119° C.; yield: 70.4% based on N-benzyloxycarbonyl-L-aspartic acid)

EXAMPLE 4

A 534 mg (2 m mol) of N-benzyloxycarbonyl-L-aspartic acid and 863 mg (4 m mol) of L-phenylalanine methyl ester hydrochloride were charged in a 30 ml flask and 8 ml of water was added to dissolve them and pH was adjusted to 6.2 with 7% ammonia water.

The resulting solution was admixed with 50 mg of Thermolysin and shaken at 38° to 40° C. over one night. The precipitate was collected and separated from the solution and dried to obtain 1,099 mg of an addition compound of N-benzyloxycarbonyl-L-aspartyl-L-phenylalanine methyl ester and L-phenylalanine methyl ester (1:1) (yield: 90.5% based on N-benzyloxycarbonyl-L-aspartic acid).

EXAMPLE 5

A 267.2 mg (1 m mol) of N-benzyloxycarbonyl-L-aspartic acid and 537.6 mg (3 m mol) of L-phenylalanine methyl ester were dissolved in 5 ml of McIlvain's buffer solution (pH: 7.0). The resulting solution was admixed with 100 mg of Thermoase and 100 mg of potato inhibitor and shaken at 38° C. for 20 hours. The precipitate was collected and washed with water and dried to obtain 580 mg of a crude crystalline addition compound of N-benzyloxycarbonyl-L-aspartyl-L-phenylalanine methyl ester and L-phenylalanine methyl ester (1:1) (melting point: 123° to 125° C.; Yield: 95.5% based on N-benzyloxycarbonyl-L-aspartic acid).

The product was dissolved in 40 ml of a solvent mixture of dimethylformamide and water (1:1) and H-form strongly acidic cation exchange resin was added to the solution under thorough stirring and then the resin was separated and the filtrate was concentrated under a reduced pressure. The residue was dissolved in dimethylformamide, and water was added to the solution to precipitate 330 mg of N-benzyloxycarbonyl-L-aspartyl-L-phenylalanine methyl ester (yield: 77.0% based on N-benzyloxy-carbonyl-L-aspartic acid; melting point 123° to 125° C.)

EXAMPLE 6

A 267.2 mg (1 m mole) of N-benzyloxycarbonyl-L-aspartic acid and 358.4 mg (2 m mol) of L-phenylalanine methyl ester were dissolved in 5 m of McIlvain's buffer solution (pH: 7.0).

The resulting solution was admixed with 100 mg of Tacynase N and 100 mg of potato inhibitor and shaken at 38° C. for 6 hours. The precipitate was collected and washed with water and dried to obtain 120 mg of a crude crystalline addition compound of N-benzyloxycarbonyl-L-aspartyl-L-phenylalanine methyl ester and L-phenylalanine methyl ester (1:1) (melting point: 119° to 123° C.; yield: 19.7%).

In accordance with the process of Example 5, the product was treated with the H-form strongly acidic cation exchange resin to obtain 50 mg of N-benzyloxycarbonyl-L-aspartyl-L-phenylalanine methyl ester (melting point: 95° to 105° C.; yield: 11.7%).

EXAMPLE 7

A 1,335 mg (5 m mol) of N-benzyloxycarbonyl-L-aspartic acid and 1,078 mg (5 m mol) of L-phenylalanine methyl ester were charged in a 30 ml flask and 4 ml of water was added to dissolve them and pH was adjusted to 6.8 with triethylamine.

The resulting solution was admixed with 20 mg of Thermolysin and shaken at 38° to 40° C. for 2 days. The precipitate was collected by a filtration and washed with 40 ml of water and dried to obtain 475 mg of an addition compound of N-benzyloxycarbonyl-L-aspartyl-L-phenylalanine methyl ester and L-phenylalanine methyl ester (1:1) (yield: 31.3% based on L-phenylalanine methyl ester hydrochloride).

The product was recrystallized from a solvent mixture of ethyl acetate and n hexane. The physical properties and results of elementary analysis of the product were as follows:

Melting point: 120° to 124° C.

$[\alpha]_D^{25}$: +7.2 (C=1, methanol)

| | Elementary analysis | | |
|---|---|---|---|
| | C | H | N |
| Calculated (%) | 63.24 | 6.13 | 6.97 |
| Found (%) | 63.52 | 6.22 | 7.04 |

EXAMPLE 8

In accordance with the process of Example 7, except adjusting pH to 5.2, the reaction and the treatment were carried out to obtain 753 mg of an addition compound of N-benzyloxycarbonyl-L-aspartyl-L-phenylalanine methyl ester and L-phenylalanine methyl ester (1:1) (yield: 49.5% based on L-phenylalanine methyl ester).

EXAMPLE 9

A 133.6 mg (0.5 m mol) of N-benzyloxycarbonyl-L-aspartic acid and 89.6 mg (0.5 m mol) of L-phenylalanine methyl ester were dissolved in 2.5 ml of McIlvain's buffer solution (pH: 7.0) with 0.07 ml of triethylamine.

The resulting solution which showed pH 6.7 was admixed with 50 mg of Thermoase and 50 mg of potato inhibitor and shaken at 38° C. for 20 hours. The precipitate was collected by a filtration and washed with water to obtain 130 mg of a crude addition compound of N-benzyloxycarbonyl-L-aspartyl-L-phenylalanine methyl ester and L-phenylalanine methyl ester (1:1) (melting point: 115° to 124° C.; yield: 85.5% based on L-phenylalanine methyl ester).

The product was dissolved in 20 ml of a solvent mixture of dimethylformamide and water (1:1) and treated with the H-form strongly acidic cation exchange resin in accordance with the process of Example 5 to obtain 75 mg of N-benzyloxycarbonyl-L-phenylalanine methyl ester (overall yield: 70% based on 50% utilization of the amount of starting L-phenylalanine methyl ester).

EXAMPLE 10

In accordance with the process of Example 9 except using 0.05 ml of N-methyl morpholine instead of 0.07 ml of triethylamine, the reaction was carried out in pH of 6.4 at the initiation to obtain 120 mg of a crystalline addition compound of N-benzyloxycarbonyl-L-aspartyl-L-phenylalanine methyl ester and L-phenylalanine methyl ester (1:1) (melting point 118° to 124° C.; yield: 78.9% based on L-phenylalanine methyl ester).

The product was treated with the H-form strongly acidic cation exchange resin in accordance with the process of Example 9 to obtain 70 mg of crystalline N-benzyloxycarbonyl-L-phenylalanine methyl ester (overall yield: 66% based on 50% utilization of the amount of starting L-phenylalanine methyl ester).

EXAMPLE 11

In accordance with the process of Example 4 except reacting at pH of 6.5 under shaking for 1 hour, the reaction was carried out to obtain 920 mg of an addition compound of N-benzyloxycarbonyl-L-aspartyl L-phenylalanine methyl ester and L-phenylalanine methyl ester (1:1). (yield: 75.8%).

EXAMPLE 12

A 534 mg (2 m mol) of N-benzyloxycarbonyl-L-aspartic acid and 863 mg (4 m mol) of L-phenylalanine methyl ester hydrochloride were charged in a 30 ml flask and 2 ml of water was added to dissolve them, and 5.5 ml of 1 N-NaOH was added to adjust pH to 7.

The resulting solution was admixed with 50 mg of Thermolysin and shaken at 38° to 40° C. for 2 hours. The precipitate was collected by a filtration and dried to obtain 734 mg of an addition compound of N-benzyloxycarbonyl-L-aspartyl-L-phenylalanine methyl ester and L-phenylalanine methyl ester (1:1) (melting point 106° to 118° C.; yield 60.5%).

EXAMPLE 13

A 540 mg (2 m mol) of N-benzyloxycarbonyl-L-aspartic acid and 863 mg (4 m mol) of L-phenylalanine methyl ester hydrochloride were charged in a 30 ml flask and 7 ml of water was added to dissolve them and pH was adjusted to 6 with 7% ammonia water.

The resulting solution was admixed with 100 mg of Thermoase and shaken at 38° to 40° C. over one night. The precipitate was washed with 70 ml of water and dried to obtain 550 mg of an addition compound of N-benzyloxycarbonyl-L-aspartyl-L-phenylalanine methyl ester (1:1) (melting point: 113° to 116° C.; yield: 45.3%).

EXAMPLE 14

A 270 mg (1 m mol) of N-benzyloxycarbonyl-L-aspartic acid and 432 mg (2 m mol) of L-phenylalanine methyl ester were charged in a 30 ml flask and 4 ml of water was added to dissolve them and pH was adjusted to 6 with 7% ammonia water.

The resulting solution was admixed with 50 mg of Thermoase and shaken at 38° to 40° C. for 40 hours. The precipitate was collected by a filtration and separated from water and dried to obtain 177 mg of an addition compound of N-benzyloxycarbonyl-L-aspartyl-L-phenylalanine methyl ester and L-phenylalanine methyl ester (1:1) (melting point: 103° to 112° C.; yield: 29.1%)

EXAMPLE 15

In accordance with the process of Example 14, except further adding 50 mg of a potato inhibitor in the solution for the reaction, the reaction was carried out to obtain 381 mg of the same product (melting point 105° to 117° C.; yield: 62.7%).

EXAMPLE 16

A 534 mg (2 m mol) of N-benzoyloxycarbonyl-L-aspartic acid and 863 mg (4 m mol) of DL-phenylalanine methyl ester hydrochloride were charged in a 30 ml flask and 7 ml of water was added to dissolve them and pH was adjusted to 6.2 with 7% ammonia water.

The resulting solution was admixed with 50 mg of Thermolysin and shaken at 38° to 40° C. over one night. The precipitate was collected by a filtration and separated from water and dried to obtain 1045 mg of crystals of an addition compound of N-benzoyloxycarbonyl-aspartylphenylalanine methyl ester and phenylalanine methyl ester (1:1) (melting point: 104° to 108° C.; yield: 86.1% based on N-benzoylcarbonyl-L-aspartic acid).

The product was recrystallized from a solvent mixture of ethyl acetate and n-hexane to obtain the product having the following physical properties and results of the elementary analysis were as follows:

Melting point: 127° to 135° C.

$[\alpha]_D^{25}$: $-6.4$ (C=1, methanol)

| Elementary analysis: $C_{32}H_{37}N_3O_9$ | | | |
|---|---|---|---|
| | C | H | N |
| Calculated (%) | 63.24 | 6.13 | 6.97 |
| Found (%) | 63.52 | 6.19 | 6.92 |

The product was assumed to the addition compound of N-benzyloxycarbonyl-L-aspartyl-L-phenylalanine methyl ester and D-phenylalanine methyl ester (1:1) because the infrared spectrum and the NMR spectrum of the product are of the same characteristics with those of Example 1.

A 800 mg of the product was dissolved in 40 ml of 1 N-HCl and extracted with 30 ml of methylene dichloride 3 times and the methylene dichloride phase was washed with water and dehydrated with anhydrous magnesium sulfate and methylene dichloride was removed by a distillation and the solid component was recrystallized from a solvent mixture of ethyl acetate and n-hexane to obtain 450 mg of crystals. The physical properties and results of elementary analysis of the product were as follows:

Melting point: 124° to 132° C.

$[\alpha]_D$: $-15.3$ (C=1 methanol)

| Elementary analysis: $C_{22}H_{24}N_2O_7$ | | | |
|---|---|---|---|
| | C | H | N |
| Calculated (%) | 61.67 | 5.65 | 6.54 |
| Found (%) | 61.38 | 5.58 | 6.29 |

The product was N-benzyloxycarbonyl-L-aspartyl-L-phenylalanine methyl ester.

The residual aqueous phase of the extraction by methylene dichloride was admixed with sodium bicarbonate to adjust pH to 8.7 and the product was extracted with 30 ml of methylene chloride 3 times. The extract was dehydrated with anhydrous magnesium sulfate and hydrogen chloride gas was fed to the extract for about 10 minutes and the methylene chloride solution was concentrated and ethyl ether was added to the solution to recrystallize the product to obtain 29.0 mg of D-phenylalanine methyl ester hydrochloride. (melting point: 149° to 151° C.; $[\alpha]_D^{25}$: $-15.1$ (C=1, methanol):

(infrared spectrum and NMR spectrum: coincident with those of L-form).

Accordingly, the assumption of the addition compound is correct. The product obtained by the reaction was the addition compound of N-benzyloxycarbonyl-L-aspartyl-L-phenylalanine methyl ester and D-phenylalanine methyl ester (1:1).

EXAMPLE 17

A 1,069 mg (4 m mol) of N-benzyloxycarbonyl-DL-aspartic acid and 863 mg (4 m mol) of L-phenylalanine methyl ester hydrochloride were charged in a 30 ml flask and 2 ml of water was added to dissolve them and pH was adjusted to 6 with 7% ammonia water.

The resulting solution was admixed with 50 mg of Thermolysin and shaken at 38° to 40° C. for 2 hours. The precipitate was collected by a filtration and washed with 20 ml of water and dried to obtain 787 mg of an addition compound of N-benzyloxycarbonyl-L-aspartyl-L-phenylalanine methyl ester and L-phenylalanine methyl ester (1:1) (melting point: 105° to 110° C.; yield; 64.8% based on N-benzyloxycarbonyl-L-aspartic acid.)

The product was recrystallized from a solvent mixture of ethyl acetate and n-hexane to obtain the product (melting point: 121° to 125° C.; $[\alpha]_D^{25}$: 7.2 (C=1, methanol).

On the other hand, N-benzyloxycarbonyl aspartic acid (mainly D-form) was recovered from the residual reaction solution.

EXAMPLE 18

Example 17 was repeated except for using DL-phenylalanine methyl ester instead of L-phenylalanine methyl ester to obtain 756 mg of an addition compound of N-benzyloxycarbonyl-L-aspartyl L-phenylalanine methyl ester and D-phenyl alanine methyl ester (1:1) (melting point: 105° to 111° C.; yield: 62.3% based on N-benzyloxycarbonyl L-aspartic acid).

The product was recrystallized from a solvent mixture of ethyl acetate and n-hexane to obtain the product (melting point: 126° to 134° C.; $[\alpha]_D^{25}$: −6.5 (C=1, methanol).

On the other hand, N-benzyloxycarbonyl aspartic acid (mainly D-form) was recovered from the residual reaction solution.

EXAMPLE 19

A 5.34 g (20 mmol) of N-benzyloxycarbonyl-L-aspartic acid and 7.53 g (42 mmol) of L-phenylalanine methyl ester were charged in a 100 ml flask and 70 ml of water was added to dissolve them. The solution having pH of 6.2 to 6.3 was obtained.

The resulting solution was admixed with 200 mg of Thermolysin and shaken at 38° to 40° C. for 4 hours. The precipitate was collected by a filtration and washed with 70 ml of water and dried to obtain 10.11 g of crystals (melting point: 117° to 120° C.). The product was confirmed to be an addition compound of N-benzyloxycarbonyl-L-aspartyl-L-phenylalanine methyl ester and L-phenylalanine methyl ester (1:1) since the product was recrystallized from a solvent mixture of ethyl acetate and n-hexane and the physical properties and results of elementary analysis of the product were as follows: Melting point: 120° to 124° C. $[\alpha]_D^{25}$: +7.2 (c=1, methanol)

| Elementary analysis: $C_{32}H_{37}N_3O_9$ | | | |
|---|---|---|---|
| | C | H | N |
| Calculated (%) | 63.24 | 6.13 | 6.97 |

| Elementary analysis: $C_{32}H_{37}N_3O_9$ -continued | | | |
|---|---|---|---|
| | C | H | N |
| Found (%) | 63.16 | 6.14 | 6.99 |

Infrared and NMR spectra showed the same characteristics mentioned above for the 1:1 addition compound of N-benzyloxycarbonyl-L-aspartyl-L-phenylalanine methyl ester with L-phenylalanine methyl ester. The product was also treated with a strong acid and extracted with an organic solvent such as ethyl acetate followed by removal of the organic solvent by distillation to obtain N-benzyloxycarbonyl-L-aspartyl-L-phenylalanine methyl ester.

A 1.00 g (1.65 mmol) of the resulting addition compound of N-benzyloxycarbonyl-L-aspartyl-L-phenylalanine methyl ester and L-phenylalanine methyl ester was charged in a 30 ml flask and 2 ml of water and 2.0 ml of 1 N-HCl were added with stirring at room temperature for 10 minutes. The resulting slurry was filtered and the precipitate was washed with 4 ml of water and dried to obtain 0.72 g of crystals of N-benzyloxycarbonyl-L-aspartyl-L-phenylalanine methyl ester (yield: 98.8%).

The resulting crystals were dissolved in ethyl acetate and n-hexane was added to recrystallize the product. The physical properties and results of elementary analysis of the final product were as follows: Melting point: 121° to 124° C. $[\alpha]_D^{25}$: −15.4 (C=1, methanol)

| Elementary analysis: $C_{22}H_{24}N_2O_7$ | | | |
|---|---|---|---|
| | C | H | N |
| Calculated (%) | 61.67 | 5.65 | 6.54 |
| Found (%) | 61.58 | 5.64 | 6.56 |

The infrared spectrum of the product coincided with that of the standard compound.

The identification of the product was also confirmed by comparing an aqueous solution of the product with that of the standard compound in a high speed liquid chromatography. The purity was measured in this method to be 100%. The apparatus and conditions in the high speed liquid chromatography analysis were as follows. This method was used for the estimation of the purities of the decomposition products of the addition compounds in the following Examples except otherwise stated. The same apparatus and conditions were used in the examples as far as this method concerned.

High speed liquid chromatography apparatus: (TSK-HLC 801 manufactured by Toyo Soda K.K.)

Column: inner diameter of 7.5 mm × length of 30 cm;

Filler: starch gel type: particle size of 5μ (TSK-GEL LS 170 manufactured by Toyo Soda K.K.).

Eluent: 0.5% aqueous solution of sodium acetate

Flow rate: 0.8 ml/min.

Pressure loss: 20 Kg/cm$^2$

Measuring temperature: room temperature

Detector: differential refractometer

EXAMPLE 20

A 1.00 g (1.65 mmol) of the addition compound of N-benzyloxycarbonyl-L-aspartyl-L-phenylalanine methyl ester and L-phenylalanine methyl ester obtained in Example 19 was charged in a 30 ml flask and 2 ml of water and 1.32 ml of 1N-HCl were added to it and the mixture was agitated at room temperature for 10 minutes and treated in the similar manners as in Example 19 to obtain 0.70 g of fine prismatic crystals having a melting point of 100° to 126° C. (content of N-benzyloxycarbonyl-L-aspartyl-L-phenylalanine methyl ester: 96.8%).

EXAMPLE 21

A 0.534 g (2 mmol) of N-benzyloxycarbonyl-L-aspartic acid and 0.86% g (4 mmol) of DL-phenylalanine methyl ester hydrochloride were charged in a 30 ml flask and 10 ml of water was added to dissolve them and pH was adjusted to 6.0 with 7% ammonia water.

The resulting solution was admixed with 50 mg of Thermolysin and shaken over one night at 38° to 40° C. The precipitate was collected and washed with 10 ml of water and dried to obtain 0.90 g of crystals having a melting point of 120° to 126° C.

A part of the crystals was recrystallized from a solvent mixture of ethyl acetate and n-hexane to obtain the product which had a melting point of 128° to 134° C. and $[\alpha]_D^{25}$ of $-6.3$ (C=1, methanol). This product gave the infrared spectrum and the NMR spectrum being substantially the same with those of the addition compound of N-benzyloxycarbonyl-L-aspartyl-L-phenylalanine methyl ester and L-phenylalanine methyl ester (1:1).

| Elementary analysis: $C_{32}H_{37}N_3O_9$ | | | |
|---|---|---|---|
| | C | H | N |
| Calculated (%) | 63.24 | 6.13 | 6.97 |
| Found (%) | 63.42 | 6.17 | 6.95 |

When the product was treated with an acid to form N-benzyloxycarbonyl-L-aspartyl-L-phenylalanine methyl ester and D-phenylalanine methyl ester at a mole ratio of 1:1.

It has been confirmed, from the results, that the resulting crystals was the addition compound of N-benzyloxycarbonyl-L-aspartyl-L-phenylalanine methyl ester and D-phenylalanine methyl ester (1:1).

A 0.50 g (0.82 mmol) of the addition compound was admixed with 4 ml of water and 0.26 g of citric acid and the mixture was agitated at room temperature for 10 minutes and treated in a similar manner as in Example 19 to obtain 0.35 g of crystals of N-benzyloxycarbonyl-L-aspartyl-L-phenylalanine methyl ester (purity 100%; yield: 99.3%).

EXAMPLE 22

A 0.50 g (0.82 mmol) of the addition compound of N-benzyloxycarbonyl-L-aspartyl-L-phenylalanine methyl ester and L-phenylalanine methyl ester obtain in Example 19 was charged in a 30 ml flask and 4 ml of water and 0.24 g (1.2 mmol) of p-toluenesulfonic acid monohydrate were added and treated by the process of Example 19 to obtain 0.33 g of crystals of N-benzyloxycarbonyl-L-aspartyl-L-phenylalanine methyl ester (purity 100%; yield: 93.6%).

EXAMPLE 23

A 0.45 g (8.2 mmol) of 85% formic acid and 8 ml of water were charged in a 30 ml flask and 0.50 g (0.82 mmol) of the addition compound of N-benzyloxycarbonyl-L-aspartyl-L-phenylalanine methyl ester and L-phenylalanine methyl ester obtained in Example 19 was added and the mixture was stirred at room temperature for 20 minutes and the product was filtered and washed with 10 ml of water and dried to obtain 0.312 g of white crystals of N-benzyloxycarbonyl-L-aspartyl-L-phenylalanine methyl ester (purity: 100%; yield: 88.6%).

EXAMPLE 24

A 0.47 g (8.2 mmol) of glacial acetic acid and 8 ml of water were charged in a 30 ml flask and 0.50 g (0.82 mmol) of the addition compound of N-benzyloxycarbonyl-L-aspartyl-L-phenylalanine methyl ester and L-phenylalanine methyl ester was added and the mixture was stirred at room temperature for 30 minutes and the product was filtered and washed with 10 ml of water and dried to obtain 0.308 g of white crystals of N-benzyloxycarbonyl-L-aspartyl-L-phenylalanine methyl ester (purity: 100%; yield: 87.2%).

EXAMPLE 25

A 1.00 g (1.65 mmol) of the addition compound of N-benzyloxycarbonyl-L-aspartyl-L-phenylalanine methyl ester and L-phenylalanine methyl ester obtained in Example 19 was charged in a 30 ml flask and 2 ml of water and 2.0 ml of 1 N-HCl were added and the mixture was stirred at 60° C. for 3 minutes and then treated in a similar manner as in Example 19 to obtain 0.35 g of crystals of N-benzyloxycarbonyl-L-aspartyl-L-phenylalanine methyl ester (purity: 100%; yield: 100%).

EXAMPLE 26

A 0.594 g (2 mmol) of N-p-methoxybenzyloxycarbonyl-L-aspartic acid and 0.860 g (4 mmol) of L-phenylalanine methyl ester hydrochloride were charged in a 30 ml flask and 1 N-NaOH was added to dissolve them and pH was adjusted to 6.0.

The resulting solution was admixed with 50 mg of Thermolysin and shaken at 38° to 40° C. over one night. The precipitate was collected by a filtration and washed with 10 ml of water and dried to obtain 0.928 g of crystals having a melting point of 68° to 74° C.

It was confirmed, from the below mentioned results, that the product was the addition compound of N-p-methoxybenzyloxycarbonyl-L-aspartyl-L-phenylalanine methyl ester and L-phenylalanine methyl ester (1:1).

The product was recrystallized from a solvent mixture of ethyl acetate and n-hexane to obtain the product. The physical properties and results of elementary analysis of the product were as follows: Melting point: 72° to 76° C. $[\alpha]_D^{25}$: +6.5 (c=1, methanol)

| Elementary analysis: $C_{33}H_{39}N_3O_{10}$ | | | |
|---|---|---|---|
| | C | H | N |
| Calculated (%) | 62.15 | 6.16 | 6.59 |
| Found (%) | 61.85 | 6.04 | 6.46 |

Infrared spectrum: $3,280^{cm-1}$ (N-H stretching vibration); 3,020 and $2,930^{cm-1}$ (C-H stretching vibration); $1,735^{cm-1}$ (C=O ester); $1,700^{cm-1}$ (C=O urethane); $1,640^{cm-1}$ (amide 1st absorption); 1,500 to $1,540^{cm-1}$ (amide 2nd absorption); $1,435^{cm-1}$ (C-H deformation vibration); $1,380^{cm-1}$ (carboxylate); 1,210 to $1,240^{cm-1}$ (C-O-C stretching vibration and amide 3rd absorption); $1,030^{cm-1}$ (phenyl in-plane vibration) and 690, 740 and $810^{cm-1}$ (phenyl out-of-plane vibration).

NMR spectrum: $\delta$(1) 2.7 ppm (2H); (2) 3.1 ppm (4H); (3) 3.6 ppm (3H) and (3.7 ppm (3H); (4) 3.8 ppm (3H); (5) 4.0 ppm (1H); (6) 4.5 ppm (1H); (7) 4.8 ppm (1H); (8)

5.0 ppm (2H); (9) 5.65 ppm (3H); (10) 5.65 ppm (1H); (11) 6.2 ppm (1H); and (12) 6.8 to 7.3 ppm (14H).

These results show that the product is the addition compound of formula (I) wherein $R_1$, $R_2$, $R_3$ and n are p-methoxybenzyloxycarbonyl, benzyl, methoxy and 1, respectively.

A 0.500 g (0.78 mmol) of the addition compound of N-p-methoxy-benzyloxycarbonyl-L-aspartyl-L-phenylalanine methyl ester and L-phenylalanine methyl ester thus obtained was charged in a 30 ml flask and 2 ml of water and 0.94 ml (0.94 mmol) of 1 N-HCl were added and the mixture was stirred at 60° C. for 3 minutes.

The resulting slurry was filtered and washed with 6 ml of water and dried to obtain 0.32 g of crystals.

It was confirmed, from the following results, that the product was N-p-methoxy-benzyloxycarbonyl-L-aspartyl-L-phenylalanine methyl ester (purity: 100%; yield: 89.1%).

The crystals were dissolved in ethyl acetate and n-hexane was added to recrystallize to obtain the product. The physical properties and results of elementary analysis of the product were as follows: Melting point: 128° to 130° C. $[\alpha]_D^{25}$: −15.1 (c=1 methanol)

| Elementary analysis: $C_{23}H_{26}N_2O_8$ | | | |
|---|---|---|---|
| | C | H | N |
| Calculated (%) | 60.25 | 5.72 | 6.11 |
| Found (%) | 60.30 | 5.74 | 5.99 |

Infrared spectrum: $3,280^{cm-1}$ (N-H stretching); 2,930 and $3,020^{cm-1}$ (C-H stretching vibration); $1,735^{cm-1}$ (C=O ester); $1,700^{cm-1}$ (C=O urethane); $1,650^{cm-1}$ (amide 1st absorption); 1,510 to $1,540^{cm-1}$ (amide 2nd absorption); $1,440^{cm-1}$ (C-H deformation); 1,220 to $1,270^{cm-1}$ (C-O-C stretching vibration, amide 3rd absorption); 1,030 and $1,050^{cm-1}$ (phenyl in-plane vibration); 690 and 810 cm$^{-1}$ (phenyl out-of-plane vibration).

NMR spectrum: δ (1) 2.8 ppm (2H); (2) 3.0 ppm (2H); (3) 3.6 ppm (3H); (4) 3.8 ppm (3H); (5) 4.5 ppm (1H); (6) 4.8 ppm (1H); (7) 5.0 ppm (2H); (8) 6.0 ppm (1H); (9) 6.6 ppm (1H); (10) 6.6 ppm (1H); (11) 6.8 to 7.3 ppm (9H).

These results show that the final product is the compound of formula (VI) wherein $R_1$, $R_2$, $R_3$ and n are p-methoxybenzyloxycarbonyl, benzyl, methoxy and 1, respectively.

A 0.2 wt. part of the resulting N-p-methoxybenzyloxycarbonyl-L-aspartyl-L-phenylalanine methyl ester was dissolved in 2 wt. parts of acetone and 1 wt. part of 4 N-HCl was added to the resulting solution and the mixture was heated on a water-bath under a mild reflux for 1.5 hours to completely decompose it to form a solution containing main components of L-aspartyl-L-phenylalanine methyl ester, L-phenylalanine methyl ester and anise alcohol from which solution, L-aspartyl-L-phenylalanine methyl ester was obtained.

EXAMPLE 27

A 0.562 g (2 mmol) of N-benzyloxycarbonyl-L-glutamic acid and 0.860 g (4 mmol) of L-phenylalanine methyl ester hydrochloride were charged in a 30 ml flask and 1 N-NaOH was added to dissolve them and pH was adjusted to 6.0.

The resulting solution was admixed with 50 mg of Thermolysin and shaken at 38° to 40° C. for one night. The precipitate was collected and washed with 10 ml of water and dried to obtain 0.510 g of crystals having a melting point of 80° C. to 85° C.

It was confirmed, from the following results, that the product was an addition compound of N-benzyloxycarbonyl-L-glutamyl-L-phenylalanine methyl ester and L-phenylalanine methyl ester (1:1).

The product was recrystallized from a solvent mixture of ethyl acetate and n-hexane to obtain the product. The physical properties and results of elementary analysis of the product were as follows: Melting point: 92° to 97° C. $[\alpha]_D^{25}$: 0.1 (C=1, methanol)

| Elementary analysis: $C_{33}H_{39}N_3O_9$ | | | |
|---|---|---|---|
| | C | H | N |
| Calculated (%) | 63.75 | 6.32 | 6.76 |
| Found (%) | 63.61 | 6.31 | 6.65 |

Infrared spectrum: $3,340^{cm-1}$ (N-H stretching vibration); 2,950 and $3,030^{cm-1}$ (C-H stretching vibration); 1,730 and $1,745^{cm-1}$ (C=O ester); $1,690^{cm-1}$ (C=O urethane); $1,660^{cm-1}$ (amide 1st absorption); $1,620^{cm-1}$ (carboxylate); $1,530^{cm-1}$ (amide 2nd absorption); $1,440^{cm-1}$ (C-H deformation vibration); $1,405^{cm-1}$ (carboxylate); 1,240 to $1,310^{cm-1}$ (C-O-C stretching vibration and amide 3rd absorption); $1,050^{cm-1}$ (phenyl in-plane vibration); 700 and $750^{cm-1}$ (phenyl out-of-plane vibration).

NMR spectrum: δ (1) 2.0 ppm (2H); (2) 2.3 ppm (2H); (3) 3.0 ppm (4H); (4) 3.6 ppm (3H) and 3.7 ppm (3H); (5) 3.8 ppm (1H); (6) 4.3 ppm (1H); (7) 4.8 ppm (1H); (8) 5.0 ppm (2H); (9) 5.8 ppm (3H); (10) 5.8 ppm (1H); (11) 7.2 ppm (1H); (12) 7.2 ppm (10H); (13) 7.3 ppm (5H).

These results show that the product is the addition compound of formula (I) wherein $R_1$, $R_2$, $R_3$ and n are benzyloxycarbonyl, benzyl, methoxy and 2, respectively.

A 0.001 g of the addition compound of N-benzyloxycarbonyl-L-glutamyl-L-phenylalanine methyl ester and L-phenylalanine methyl ester was added to 2.3 ml (0.32 mmol) of 0.14 N-HCl under stirring in a 15 ml test tube and the mixture was further stirred at room temperature for 15 minutes.

The resulting white precipitate was filtered and washed with 3 ml of water and dried to obtain 0.683 g of crystals.

It was confirmed from the following results that the product was N-benzyloxycarbonyl-L-glutamyl-L-phenylalanine methyl ester (purity: 100%; yield: 95.8%).

The crystals were dissolved in ethyl acetate and n-hexane was added to recrystallize to obtain the product.

The physical properties and results of elementary analysis of the product were as follows: Melting point: 97° to 99° C. $[\alpha]_D^{25}$: −11.0 (C=1, methanol)

| Elementary analysis: $C_{23}H_{26}N_2O_7$ | | | |
|---|---|---|---|
| | C | H | N |
| Calculated (%) | 62.43 | 5.92 | 6.33 |
| Found (%) | 62.63 | 5.94 | 6.24 |

Infrared spectrum: $3,300^{cm-1}$ (N-H stretching vibration); 2,930 and $3,030^{cm-1}$ (C-H stretching vibration); $1,735^{cm-1}$ (C=O ester); $1,890^{cm-1}$ (C=O urethane); $1,650^{cm-1}$ (amide 1st absorption); $1,530^{cm-1}$ (amide 2nd absorption); $1,440^{cm-1}$ (C-H deformation vibration); 1,220 to $1,280^{cm-1}$ (C-O-C stretching vibration and amide 3rd absorption); 1,050$cm^{-1}$ (phenyl in-plane vibration) 695 and 735$cm^{-1}$ (phenyl out-of-plane vibration).

NMR spectrum: δ (1) 2.0 ppm (2H); (2) 2.4 ppm (2H); (3) 3.1 ppm (2H); (4) 3.7 ppm (3H); (5) 4.3 ppm (1H); (6) 4.8 ppm (1H); (7) 5.1 ppm (2H); (8) 5.9 ppm (1H); (9) 7.2 ppm (1H); (10) 7.2 ppm (5H); (11) 7.3 ppm (5H); (12) 8.1 ppm (1H).

These results show that the final product is the compound of formula (VI) wherein $R_1$, $R_2$, $R_3$ and n are benzyloxycarbonyl, benzyl, methoxy and 2, respectively.

The resulting N-benzyloxycarbonyl-L-glutamyl-L-phenylalanine methyl ester could be converted by a reduction with hydrogen to L-glutamyl-L-phenylalanine methyl ester and it could be also converted by a hydrolysis to N-benzyloxycarbonyl-L-glutamyl-L-phenylalanine.

EXAMPLE 28

A 0.686 g (3.12 mmol) of L-phenylalanine methyl ester hydrochloride was charged in a 100 ml flask and 25 ml of water was added to dissolve it, and 2 N-NaOH aqueous solution was added to the solution under cooling with ice and stirring it to give pH 7.5, and 0.360 g (1.44 mmol) of N-benzyloxycarbonyl-L-aspartic acid anhydride was gradually added to the solution under stirring and maintaining pH to 7.0 to 7.5 by adding 2 N-NaOH aqueous solution. After the addition, the mixture was further stirred for 2 hours and 1 N-HCl aqueous solution was added to the reaction mixture to give pH 6. The resulting precipitate was collected by a filtration and washed with 50 ml of water and dried to obtain 0.416 g of an addition compound of N-benzyloxycarbonyl-L-aspartylphenylalanine methyl ester (a mixture of 86% of N-benzyloxycarbonyl-L-aspartyl-($C_{60}$)-L-phenylalanine methyl ester and 14% of N-benzyloxycarbonyl-L-aspartic-($C_\beta$)-L-phenylalanine methyl ester) and L-phenylalanine methyl ester (1:1) (melting point: 108° to 115° C.). In the reaction, a considerable amount of N-benzyloxycarbonyl-L-aspartyl-($C_\beta$)-L-phenylalanine methyl ester was produced, but most of the compound was remained in the filtrate and washing water.

In a 12 ml beaker, 0.200 g (0.329 mmol) of the resulting addition compound of N-benzyloxycarbonyl-L-aspartyl-($C_\alpha$ and $C_\beta$)-L-phenylalanine methyl ester and L-phenylalanine methyl ester was added to 1.7 ml (0.7 mmol) of 0.4 N-HCl aqueous solution under stirring and the mixture was further stirred at room temperature for 15 minutes.

The resulting white precipitate was filtered and washed with 3 ml of water and dried to obtain 0.136 g (yield: 96.3%) of crystals of N-benzyloxycarbonyl-L-aspartyl-L-phenylalanine methyl ester (containing 17% of N-benzyloxycarbonyl-L-aspartyl-($C_\beta$)-L-phenylalanine methyl ester) (melting point 110° C. to 118° C.).

EXAMPLE 29

In a 30 ml flask, 0.543 g (2 mmol) of N-benzyloxycarbonyl-L-aspartic acid and 0.918 g (4 mmol) of L-phenylalanine ethyl ester hydrochloride were dissolved in 5 ml of water, and 4 N-NaOH aqueous solution was added to adjust pH 6.

The resulting solution was admixed with 50 mg of Thermolysin and the mixture was shaken at 38° to 40° C. over one night. The precipitate was collected by a filtration and washed with 30 ml of water and dried to obtain 0.913 g of crystals having a melting point of 85° to 90° C.

The product was confirmed to be the addition compound of N-benzyloxycarbonyl-L-aspartyl-L-phenylalanine ethyl ester and L-phenylalanine ethyl ester (1:1).

The product was recrystallized from a solvent mixture of ethyl acetate and n-hexane and the physical properties and results of elementary analysis of the product were as follows: Melting point: 93° to 95° C. $[\alpha]_D^{25}$: +6.0 (C=1, methanol)

| Elementary analysis: $C_{34}H_{41}N_3O_9$ | | | |
|---|---|---|---|
| | C | H | N |
| Calculated (%) | 64.23 | 6.50 | 6.61 |
| Found (%) | 64.50 | 6.56 | 6.63 |

Infrared spectrum: 3,300 cm$^{-1}$ (N-H stretching vibration); 2,900 to 3,050 cm$^{-1}$ (C-H stretching vibration); 1,710 to 1,740 cm$^{-1}$ (C=O ester and C=O urethane); 1,640 cm$^{-1}$ (amide 1st absorption); 1,585 cm$^{-1}$ (carboxylate); 1,520 cm$^{-1}$ (amide 2nd absorption); 1,440 cm$^{-1}$ (C-H deformative vibration); 1,380 cm$^{-1}$ (carboxylate); 1,200,1,270 cm$^{-1}$ (C-O-C stretching vibration and amide 3rd absorption); 1,055 cm$^{-1}$ (phenyl in-plane vibration); 700,730 and 750 cm$^{-1}$ (phenyl out-of-plane vibration).

NMR spectrum: δ (1) 1.1 ppm (6H); (2) 2.7 ppm (2H); (3) 3.0 ppm (4H); (4) 4.0 ppm (4H); (5) 4.1 ppm (1H); (6) 4.5 ppm (1H); (7) 4.7 ppm (1H); (8) 5.0 ppm (2H); (9) 6.2 ppm (1H); (10) 6.7 ppm (3H); (11) 7.2 ppm (1H); (12) 7.2 ppm (10H); (13) 7.3 ppm (5H).

These results show that the product is the addition compound of formula (1) wherein $R_1, R_2, R_3$ and n are benzyloxycarbonyl, benzyl, ethoxy and 1.

In a 30 ml flask, 0.125 g (0.197 mmol) of the resulting addition compound of N-benzyloxycarbonyl-L-aspartyl-L-phenylalanine ethyl ester and L-phenylalanine ethyl ester was admixed with 2 ml of water and 0.24 ml of 1 N-HCl (0.24 mmol) and the mixture was stirred at room temperature for 30 minutes. The resulting slurry was filtered and the product was washed with 5 ml of water and dried to obtain 0.0807 g of crystals of N-benzyloxycarbonyl-L-aspartyl-L-phenylalanine ethyl ester (purity: 100%; yield: 92.6%). The crystals were recrystallized from a solvent mixture of ethyl acetate and n-hexane to obtain the product. The physical properties and results of elementary analysis of the product were as follows. Melting point: 128° to 135° C. $[\alpha]_D^{25}$: −17.3 (C=1, methanol)

| Elementary analysis: $C_{23}H_{26}N_2O_7$ | | | |
|---|---|---|---|
| | C | H | N |
| Calculated (%) | 62.43 | 5.92 | 6.33 |
| Found (%) | 62.82 | 5.96 | 6.40 |

Infrared spectrum: 3,300 cm$^{-1}$; 2,900 to 3,100 cm$^{-1}$; 1,730 cm$^{-1}$; 1,690 cm$^{-1}$; 1,655 cm$^{-1}$; 1,530 cm$^{-1}$; 1,440 cm$^{-1}$; 1,200 to 1,280 cm$^{-1}$ 1,030 cm$^{-1}$; 690 cm$^{-1}$; 740 cm$^{-1}$.

NMR spectrum: δ 1.1 ppm; 2.8 ppm; 3.0 ppm; 4.1 ppm; 4.6 ppm; 4.8 ppm; 5.1 ppm; 6.0 ppm; 7.1 ppm; 7.3 ppm; 9.6 ppm.

EXAMPLE 30

A 5.00 g (16.82 mmol) of N-p-methoxy-benzyloxycarbonyl-L-aspartic acid and 7.26 g (33.64 mmol) of L-phenylalanine methyl ester hydrochloride were charged in a 100 ml flask and 1 N-NaOH aqueous solution was added to dissolve them and pH was adjusted to 6.0.

The resulting solution was admixed with 2.0 g of Thermolysin and 0.4 g of potato inhibitor and shaken at 38° to 40° C. for 5 hours. The precipitate was collected by a filtration and washed with 100 ml of water and dried to obtain 8.11 g of crystals having a melting point of 88° to 92° C. (yield: 75.6% as the addition compound of N-p-methoxybenzyloxycarbonyl-aspartyl-phenylalanine methyl ester and phenylalanine methyl ester (1:1)).

The product was recrystallized from a solvent mixture of ethyl acetate and n-hexane and the resulting crystals showed the physical characteristics and the results of elementary analysis both substantially identical with those of the addition compound prepared in Example 26.

A 0.3 g of the addition compound of N-p-methoxybenzyloxycarbonyl-L-aspartyl-L-phenylalanine methyl ester and L-phenylalanine methyl ester was charged in 20 ml flask and 3 ml of acetone was added to dissolve it and 2 ml of 2.4 N-HCl was added to react them at 60° C. for 1 hour.

A portion of the reaction mixture was admixed with water, 1.2 N-NaHCO₃ aqueous solution and cyclohexanone as an internal standard to prepare the sample, and the conversion to α-L-aspartyl-L-phenylalanine methyl ester was confirmed by the high speed liquid chromatography. The yield was 72.7%.

EXAMPLE 31

A 0.3 g of the addition compound of N-p-methoxybenzyloxycarbonyl-L-aspartyl-L-phenylalanine methyl ester and L-phenylalanine methyl ester which was obtained in Example 30 was charged in a 20 ml flask.

In accordance with the process of Example 30 except using dioxane instead of acetone, the decomposition of the addition compound and the analysis of the product were carried out.

The yield of α-L-aspartyl-L-phenylalanine methyl ester was 73.0%.

EXAMPLE 32

The process of Example 31 was repeated except using methanol instead of dioxane. The yield of α-L-aspartyl-L-phenylalanine methyl ester was 63.3%.

EXAMPLE 33

The process of Example 31 was repeated except using N,N-dimethylformamide instead of dioxane. The yield of α-L-aspartyl-L-phenylalanine methyl ester was 28.1%.

EXAMPLE 34

The process of Example 31 was repeated except using 4 ml of dioxane, 1 ml of HCl-dioxane solution (5.3 N) and triethylamine as a neutralizing agent instead of 3 ml of dioxane, 2 ml of 2.4 N-HCl and 1.2 N-NaHCO₃ aqueous solution, respectively. The yield of α-L-aspartyl-L-phenylalanine methyl ester was 98.6%.

EXAMPLE 35

The process of Example 34 was repeated except reacting at 90° C. for 20 minutes instead of at 60° C. for 1 hour. The yield of α-L-aspartyl-L-phenylalanine methyl ester was 88.5%.

EXAMPLE 36

The process of Example 34 was repeated except using 4.5 ml of dioxane and 0.5 ml of HCl-dioxane solution (5.3 N) instead of 4 ml and 1 ml, respectively thereof and also except reacting at 90° C. instead of 60° C. The yield of α-L-aspartyl-L-phenylalanine methyl ester was 84.4%.

EXAMPLE 37

The process of Example 34 was repeated except using 3 ml of dioxane and 2 ml of HCl-dioxane solution (5.3 N) instead of 4 ml and 1 ml, respectively thereof and also except reacting at 30° C. for 120 minutes instead of at 60° C. for 1 hour. The yield of α-L-aspartyl-L-phenylalanine methyl ester was 98.6%.

EXAMPLE 38

The process of Example 34 was repeated except using 4.5 ml of dioxane and 0.5 ml of 60% perchloric acid instead of 4 ml of dioxane and 1 ml of the HCl-dioxane solution (5.3 N), respectively. The yield of α-L-aspartyl-L-phenylalanine methyl ester was 65.5%.

EXAMPLE 39

The process of Example 34 was repeated except using 4.85 ml of dioxane and 0.15 of conc. sulfuric acid instead of 4 ml of dioxane and 1 ml of the HCl-dioxane solution (5.3 N). The yield of α-L-aspartyl-L-phenylalanine methyl ester was 89.9%.

EXAMPLE 40

A 0.3 g of the addition compound of N-p-methoxybenzyloxycarbonyl-L-aspartyl-L-phenylalanine methyl ester and L-phenylalanine methyl ester (1:1) which was obtained in Example 30 was dissolved in 2 ml of dioxane and then 3 ml of trifluoroacetic acid was added to react them at 60° C. for 1 hour.

The reaction mixture was subjected to the evaporation under a reduced pressure and then, water, triethylamine and cyclohexanone as an internal standard were added to a portion thereof to prepare a sample, and the sample was analyzed by the high speed liquid chromatography. The yield of α-L-aspartyl-L-phenylalanine methyl ester was 96.4%.

EXAMPLE 41

A 1,000 g of the addition compound of N-p-methoxybenzyloxycarbonyl-L-aspartylL-phenylalanine methyl ester and L-phenylalanine methyl ester (1:1) which was obtained in Example 30, 14 ml of dioxane and 4 ml of HCl-dioxane solution (5.3 N) were charged in a 50 ml flask and the mixture was stirred at 60° C. for 1 hour to react them. Dioxane was distilled off from the reaction mixture under a reduced pressure and 6 ml of water and 20 ml of diethyl ether were added to the remained oily product to mix them under stirring and then the two phases were separated. 10 Ml of diethyl ether was further added to the aqueous phase to extract the product in a similar way as above. The last said extraction was repeated for 3 times.

The diethyl ether phases were collected and washed with 5 ml of 5% aqueous solution of sodium bicarbonate for 2 times, and dehydrated with anhydrous magnesium sulfate. Diethyl ether was distilled off under a reduced pressure to obtain 0.176 g (yield 81.2%) of crude anise alcohol.

The aqueous phase was neutralized with 7% aqueous solution of sodium hydroxide of pH of 6 and it was kept at about 5° C. over one night. The resulting precipitated crystals were filtered and washed with 2 ml of water and dried to obtain 0.316 g (yield 68.5%) of crude L-aspartyl-L-phenylalanine methyl ester.

The filtrate with the washing water fraction was alkalized with 7% aqueous solution of sodium hydroxide to pH of 9 and the product was extracted with 15 ml of dichloromethane for 3 times. The dichloromethane phases were collected and washed with 5 ml of water and dehydrated with anhydrous magnesium sulfate. Dichloroethane was distilled off under a reduced pressure to obtain 0.234 g (yield 83.4%) of crude L-phenylalanine methyl ester.

EXAMPLE 42

A 1.189 g (4 mmol) of N-p-methoxybenzyloxycarbonyl-L-aspartic acid and 1.837 g (8 mmol) of L-phenylalanine ethyl ester hydrochloride were charged in a 30 ml flask and dissolved with the addition of 1 N-NaOH aqueous solution to adjust pH 6.0.

Water was added to the solution to give 15 ml of the aqueous solution. The resulting solution was admixed with 0.1 g of Thermolysin and the mixture was stirred at 38° to 40° C. for 7 hours.

The resulting precipitate was collected by a filtration and washed with 30 ml of water and dried to obtain 2.401 g (yield 90.2%) of the addition compound of N-p-methoxybenzyloxycarbonyl-L-aspartyl-L-phenylalanine ethyl ester and L-phenylalanine ethyl ester (1:1). This was confirmed by the below metnioned analyses.

The product was recrystallized from a solvent mixture of methanol and diethylether. The physical characteristics and results of elementary analysis of the product were as follows:

Melting point; 82° to 87° C. $[\alpha]_D^{25}$; +6.0 (C=1, methanol)

| Elementary analysis: ($C_{35}H_{43}N_3O_{10}$) | | | |
|---|---|---|---|
| | C | H | N |
| Calculated (%) | 63.14 | 6.51 | 6.31 |
| Found (%) | 63.52 | 6.57 | 6.54 |

Infrared and NMR spectra showed the following characteristic absorptions:

Infrared spectrum: 3,300 $cm^{-1}$ (N-H stretching vibration); 2,900 to 3,050 $cm^{-1}$ (C-H stretching vibration); 1,720, 1,730 and 1,740 (C=O esters and urethane); 1,650 $cm^{-1}$ (amide 1st absorption); 1,510 to 1540 $cm^{-1}$ (amide 2nd absorption); 1,440 $cm^{-1}$ (C-H deformation vibration); 1,390 $cm^{-1}$ (carboxylate); 1,220 to 1,280 $cm^{-1}$ (C-O stretching and amide 3rd absorption); 1,030 $cm^{-1}$ (phneyl plane deformation); and 690, 760 and 810 $cm^{-1}$ (phenyl out-of-plane vibration).

NMR Spectrum ($\delta$ value): (1) 1.2 ppm (6H); (2) 2.7 ppm (2H); (3) 3.1 ppm (4H); (4) 3.8 ppm (3H); (5) 4.0 ppm (4H); (6) 4.1 ppm (1H); (7) 4.5 ppm (1H); (8) 4.7 ppm (1H); (9) 5.0 ppm (2H); (10) 5.5 ppm (4H); (11) 6.1 ppm (1H); (12) 6.8-7.4 ppm (14H).

These results show that the product is the addition compound of formula (I) wherein $R_1$, $R_2$, $R_3$ and n are p-methoxybenzyloxycarbonyl, benzyl, ethoxy and 1, respectively.

The process of Example 34 was repeated except using the resulting addition compound instead of the addition compound of N-p-methoxycarbonyl-L-aspartyl-L-phenylalanine methyl ester with L-phehylalanine methyl ester to produce L-aspartyl-L-phenylalanine ethyl ester. The yield of α-L-aspartyl-L-phenylalanine ethyl ester was 95.5%.

EXAMPLE 43

A 1.189 g (4 mmol) of N-p-methoxybenzyloxycarbonyl-L-aspartic acid and 1.725 g (8 mmol) of D L-phenylalanine methyl ester hydrochloride were charged in a 30 ml flask and dissolved with the addition of 1 N-NaOH aqueous solution to adjust pH 6.0. Water was added to the solution to give 13 ml of the aqueous solution. The resulting solution was admixed with 0.1 g of Thermolysin and the mixture was stirred at 38° to 40° C. for 50 minutes.

The precipitate was collected by a filtration and washed with 30 ml of water and dried to obtain 2.109 g of crystals having a melting point of 119° to 128° C. and the product were recrystallized from a solvent mixture of ethyl acetate and n-hexane and dried at 80° C. for 7 hours under a reduced pressure. The product was confirmed to be the addition compound of N-p-methoxybenzyloxycarbonyl-L-aspartyl-L-phenlalanine methyl ester and D-phenylalanine methyl ester (1:1) semihydrate by the below mentioned analyses.

Physical characteristics and results of elementary analysis were as follows:

Melting point; 131° to 133° C. $[\alpha]_D^{25}$; −4.2 (C=1, methanol)

| Elementary analysis: ($C_{33}H_{39}N_3O_{10}\cdot\frac{1}{2}H_2O$) | | | |
|---|---|---|---|
| | C | H | N |
| Calculated (%) | 61.29 | 6.23 | 6.50 |
| Found (%) | 61.50 | 6.12 | 6.49 |

Infrared and NMR spectra showed the same characteristic features as in the addition compound of formula (1) prepared in Example 26 wherein $R_1$, $R_2$, $R_3$ and n were p-methoxybenzyloxycarbonyl, benzyl, methoxy and 1, respectively, except that absorption due to protons of water and due to protons of —NH— and $NH_3^+$- groups shifted to 4.1 ppm by the disturbance caused by the presence of water because the product includes crystallization water as explained below. A 1.5024 sample of the product was heated under microwave irradiation for 12 minutes in a microwave heater of 2.45 GHz in frequency and 1.2 KW in power to dry the sample, whose weight was reduced to 1.48152 g after the irradiation (loss on drying: 0.02091 g). Elementary analysis of the irradiated sample gave the following results:

| | C | H | N |
|---|---|---|---|
| Calculated values for $C_{33}H_{39}N_3O_{10}$ (%) | 62.15 | 6.16 | 6.69 |
| Found (%) | 62.07 | 6.17 | 6.69 |

Infrared and NMR spectra of the irradiated sample gave the same characteristic features as in the addition compound of formula (1) prepared in Example 26.

A 1.0 g amount of the irradiated sample was admixed with 4 ml of water and 2 ml of 1 N-HCl and then the resulting mixture was agitated at 60° C. for 3 minutes. After solid-liquid separation of the resulting slurry, N-p-methoxycarbonyl-L-phenylalanine methyl ester and D-phenylalanine methyl ester were recovered in the 1:1 molar ratio from the solid phase and the liquid phase, respectively.

The process of Example 34 was repeated except using 0.3 g of the resulting addition compound (semihydrate instead of the addition compound obtained in Example 30). The yield of α-L-aspartyl-L-phenylalanine methyl ester and D-phenylalanine methyl ester were 95.9%.

EXAMPLE 44

A 0.3 g of the addition compound of N-p-methoxybenzyloxycarbonyl L-aspartyl-L-phenylalanine methyl ester and L-phenylalanine methyl ester (1:1) obtained in Example 30 was dissolved in 10 ml of HCl-chloroform solution (0.31 N) to react them at 60° C. for 2 hours. The reaction mixture was treated under a reduced pressure to distill off the volatile matters, and then, water, triethylamine and cyclohexanone as the internal standard were added to the residue to prepare a sample, and the sample was analyzed by the high speed liquid chromatography. The yield of α-L-aspartyl-L-phenylalanine methyl ester was 94.3%.

What is claimed is:

1. A process for resolving a racemate of a phenylalanine lower alkyl ester, comprising:

(a) preparing an addition compound of the formula:

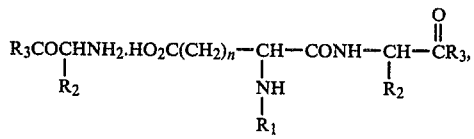

wherein the

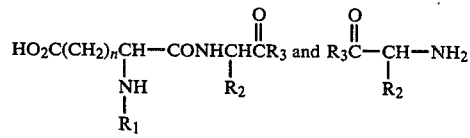

fragments of said addition compound are the LL form and D form respectively, and wherein $R_1$ is a benzyloxycarbonyl group or a p-methoxybenzyloxycarbonyl group, $R_2$ is benzyl, $R_3$ is lower alkoxy and n is 1 or 2 by reacting an N-substituted-L-monoamino-dicarboxylic acid of the formula:

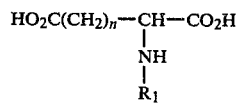

wherein $R_1$ and n are as defined above with a DL-phenylalanine lower alkyl ester of the formula:

wherein $R_2$ and $R_3$ are as defined above in the presence of protease in an aqueous medium at a pH at which said protease exerts its enzymatic activity;

(b) separating said addition compound from the aqueous medium;

(c) reacting said acid addition compound with an aqueous acid solution, thereby decomposing said acid addition compounds; and (d) recovering said phenylalanine lower alkyl ester in its D-form.

2. The process of claim 1, wherein the value of n in said acid addition compound is one.

3. The process of claim 1, wherein after decomposing said acid addition compounds, said D-phenylalanine lower alkyl ester is recovered by extracting the aqueous phase with a water immiscible organic solvent with the pH of the aqueous phase being adjusted to a pH of 5 to 6, allowing the dipeptide ester product to settle from solution and filtering the settled material, adjusting the pH of the aqueous phase to a pH of 8 to 10, and recovering the organic solvent phase containing the free phenylalanine lower alkyl ester.

4. A process for producing a dipeptide ester having the formula:

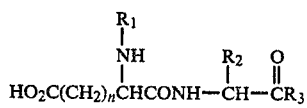

wherein $R_1$ is an aliphatic oxycarbonyl group, a benzyloxycarbonyl group, optionally substituted, a benzoyl group, an aromatic sulfonyl group or a sulfinyl group, $R_2$ is methyl, isopropyl, isobutyl, isoamyl or benzyl, $R_3$ is lower alkoxyl, benzyloxy or benzhydryloxy and n is 1 or 2, which comprises:

(a) reacting an N-substituted monoaminodicarboxylic acid of the formula:

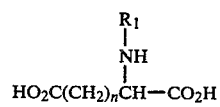

wherein $R_1$ and n are as defined above with an amino carboxylic acid ester of the formula:

in an aqueous medium in the presence of protease at a pH at which said protease exerts its enzymatic activity, thereby depositing an addition compound of the formula:

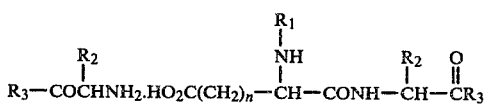

wherein $R_1$ to $R_3$ and n are as defined above;

(b) separating said addition compound from said aqueous medium;

(c) reacting said addition compound with an acid to decompose the same; and (d) recovering the dipeptide ester component from the acid addition compound.

5. The process of claim 4, which further comprises dissolving said acid addition compound in an organic solvent prior to reaction of the same with acid in step (c).

6. The process of claim 5, wherein said organic solvent is a ketone, a cyclic ether, a chlorinated hydrocarbon, a non-protic polar organic solvent, an ester or an alcohol.

7. The process of claim 4, wherein said acid is added to said addition compound in step (c) as an aqueous solution, and the liberated dipeptide ester is recovered as a solid.

8. The process of claim 5, wherein said acid reacted with said addition compound in step (c) is in the form of an aqueous solution, and said dipeptide ester is recovered from the organic solvent phase.

9. The process of claim 5, wherein said acid is a cation exchange resin in the $H^+$-form.

* * * * *

UNITED STATES PATENT AND TRADEMARK OFFICE
CERTIFICATE OF CORRECTION

PATENT NO. : 4,436,925
DATED      : March 13, 1984
INVENTOR(S): Yoshikazu Isowa et al It is certified that error appears in the above-identified patent and that said Letters Patent is hereby corrected as shown below:

On the title page, Items [22] and [75] should read as follows:

--[22] Jun. 3, 1982 --

--[75] Yoshikazu Isowa; Muneki Ohmori, both of Tokyo; Kaoru Mori; Tetsuya Ichikawa, both of Sagamihara; Yuji Nonaka, Shin-Nanyo; Keiichi Kihara, Shin-Nanyo; Kiyotaka Oyama, Shin-Nanyo; Heijiro Satoh, Shin-Nanyo; Shigeaki Nishimura, Shin-Nanyo, all of Japan --

Signed and Sealed this

Twentieth Day of November 1984

[SEAL]

Attest:

GERALD J. MOSSINGHOFF

Attesting Officer

Commissioner of Patents and Trademarks

UNITED STATES PATENT AND TRADEMARK OFFICE
CERTIFICATE OF CORRECTION

PATENT NO. : 4,436,925
DATED : March 13, 1984
INVENTOR(S) : Isowa, Yoshikazu; Ohmori, Muncki; Mori, Kaoru; et al.

It is certified that error appears in the above-identified patent and that said Letters Patent is hereby corrected as shown below:

ON THE TITLE PAGE

Under the heading "Assignees" change "Sajami" to --Sagami--.

Under the heading "ABSTRACT" change "have" to --having--.

Also under the heading "ABSTRACT", in the first formula (I), insert a vertical line between "CH" (first occurrence) and the $R_2$ beneath the "CH".

Also under the heading "ABSTRACT", in the line between formulas (IV) and (V), change "carboxlic" to --carboxylic--.

Also, please make the following changes:

| Col. | Line | | |
|---|---|---|---|
| 1 | 40 | Change "Autumun" to | --Autumn--. |
| 1 | 41 | Change "(1976)." to | --(1976)).-- |
| 1 | 48 | Change "aminoacids" to | --amino acids--. |
| 1 | 61 | Change "counter part" to | --counterpart--. |

UNITED STATES PATENT AND TRADEMARK OFFICE
CERTIFICATE OF CORRECTION

PATENT NO. : 4,436,925

DATED : March 13, 1984

INVENTOR(S) : Isowa, Yoshikazu; Ohmori, Muncki; Mori, Kaoru; et al.

It is certified that error appears in the above-identified patent and that said Letters Patent is hereby corrected as shown below:

| Col. | Line | |
|---|---|---|
| 3 | 55 | Change "Aspartyl" to --aspartyl--. |
| 3 | 56 | Delete "of" (second occurrence). |
| 3 | 57 | Change "it's" to --its--. |
| 3 | 62 | Change "n-1" to --n=1--. |
| 4 | 22 | Change "$(C_4H_9O—),$" to --$(C_4H_9O—)$;--. |
| 4 | 25 | Change "bonyl:" to --bonyl;--. |
| 4 | 26 | Change "benzyl:" to --benzyl; and--. |
| 4 | 52 | Change "(3H) 3.7" to --(3H) to 3.7--. |
| 4 | 60 | Change "benzyl oxycarbonyl," to --benzyloxycarbonyl,--. |
| 5 | 2 | Before "same" insert --the--. |
| 5 | 37 | Before "such" insert --acid--. |
| 5 | 65 | Delete "of the" (first occurrence). |
| 6 | 11 | Before "amino" insert --the--. |
| 6 | 16 | Change "to" to --on--. |

UNITED STATES PATENT AND TRADEMARK OFFICE
CERTIFICATE OF CORRECTION

PATENT NO. : 4,436,925
DATED : March 13, 1984
INVENTOR(S) : Isowa, Yoshikazu; Ohmori, Muncki; Mori, Kaoru; et al.

It is certified that error appears in the above-identified patent and that said Letters Patent is hereby corrected as shown below:

| Col. | Line | |
|---|---|---|
| 6 | 18 | Change "t," to --it,--. |
| 6 | 24 | Change "convention" to --conventional--. |
| 7 | 24 | Change "depending" to --dependent--. |
| 7 | 63 | Change "occurrs" to --occurs--. |
| 8 | 6 | Before "performed" insert --is--. |
| 8 | 9 | Change "is" to --are--. |
| 8 | 13 | Change "Thus" to --The--. |
| 8 | 26 | Before "acid" (second occurrence) insert --amino--. |
| 8 | 47 | Change "mentioned-above" to --mentioned above--. |
| 9 | 46 | Before "ratio" insert --a--. |
| 10 | 28 | Change "solvents especially," to --solvents, especially--. |
| 11 | 15 | Change "chose" to --choose--. |

UNITED STATES PATENT AND TRADEMARK OFFICE
CERTIFICATE OF CORRECTION

PATENT NO. : 4,436,925  
DATED : March 13, 1984  
INVENTOR(S) : Isowa, Yoshikazu; Ohmori, Muncki; Mori, Kaoru; et al.

Page 4 of 7

It is certified that error appears in the above-identified patent and that said Letters Patent is hereby corrected as shown below:

| Col. | Line | |
|---|---|---|
| 11 | 22 | Change "amounts" to --amount--. |
| 11 | 26 | Change "phases of the" to --phases, --. |
| 12 | 28 | Before "elementary" insert --of--. |
| 12 | 51 | Change "benzyloxycarbonyl L-aspartyl" to --benzyloxycarbonyl-L-aspartyl--. |
| 12 | 53 | Before "NMR" insert --the--. |
| 15 | 17 | Change "asparty L-" to --aspartyl-L- --. |
| 15 | 19 | Change "(1:1)." to --(1:1)--. |
| 16 | 33 | Change "with" to --as--. |
| 16 | 35 | Change "A 800 mg" to --An 800 mg amount--. |
| 16 | 65 | Change "hydrochloride." to --hydrochloride--. |
| 17 | 33 | Change "aspartyl L-phenylalanine" to --aspartyl-L-phenylalanine--. |
| 17 | 34 | Change "D-phenyl alanine" to --D-phenylalanine--. |

UNITED STATES PATENT AND TRADEMARK OFFICE
CERTIFICATE OF CORRECTION

PATENT NO. : 4,436,925

DATED : March 13, 1984

INVENTOR(S) : Isowa, Yoshikazu; Ohmori, Muncki; Mori, Kaoru; et al.

It is certified that error appears in the above-identified patent and that said Letters Patent is hereby corrected as shown below:

| Col. | Line | |
|---|---|---|
| 17 | 36 | Change "benzyloxycarbonyl L-aspartic" to --benzyloxycarbonyl-L-aspartic--. |
| 17 | 49 | Change "The" to --A--. |
| 17 | 62 | Change "(c=1," to --(C=1,--. |
| 18 | 48 | Before "otherwise" insert --as--. |
| 18 | 50 | Before "concerned" insert --is--. |
| 19 | 1 | Change "the similar manners" to --a similar manner--. |
| 19 | 22 | Change "being" to --as--. |
| 19 | 23 | Change "with" to --as--. |
| 19 | 39 | Change "was" to --were--. |
| 19 | 53 | Change "obtain" to --obtained--. |
| 20 | 49 | Change "(c=1," to --(C=1,--. |
| 21 | 25 | Change "(c=1" to --(C=1--. |
| 21 | 67 | Change "shaked" to --shaken--. |

UNITED STATES PATENT AND TRADEMARK OFFICE
CERTIFICATE OF CORRECTION

PATENT NO. : 4,436,925    Page 6 of 7
DATED : March 13, 1984
INVENTOR(S) : Isowa, Yoshikazu; Ohmori, Muncki; Mori, Kaoru; et al.

It is certified that error appears in the above-identified patent and that said Letters Patent is hereby corrected as shown below:

| Col. | Line | |
|---|---|---|
| 22 | 65 | Change "1,890" to --1,690--. |
| 23 | 2 | Change "bration)" to --bration);--. |
| 23 | 36 | Change "($C_{60}$)" to --($C_\alpha$)--. |
| 23 | 43 | Delete "was". |
| 23 | 64 | Before "pH" insert --to--. |
| 24 | 36 | Change "(1)" to --(I)--. |
| 25 | 27 | Change "in 20 ml" to --into a 20 ml--. |
| 26 | 65 | Change "10 Ml" to --10 ml--. |
| 26 | 68 | Delete "for". |
| 27 | 3 | Delete "for". |
| 27 | 8 | Change "of" (second occurrence) to --to--. |
| 27 | 16 | Delete "for". |
| 27 | 28 | Before "pH" insert --to--. |
| 27 | 39 | Change "metnioned" to --mentioned--. |
| 27 | 62 | Change "(phneyl" to --(phenyl--. |

UNITED STATES PATENT AND TRADEMARK OFFICE
CERTIFICATE OF CORRECTION

PATENT NO. : 4,436,925

DATED : March 13, 1984

INVENTOR(S) : Isowa, Yoshikazu; Ohmori, Muncki; Mori, Kaoru; et al.

It is certified that error appears in the above-identified patent and that said Letters Patent is hereby corrected as shown below:

| Col. | Line | |
|---|---|---|
| 28 | 8 | Change "L-phehylalanine" to --L-phenylalanine--. |
| 28 | 15 | Change "D" to --D,--. |
| 28 | 18 | Before "pH" insert --to--. |
| 28 | 26 | Change "were" to --was--. |
| 28 | 30 | Change "phenlalanine" to --phenylalanine--. |
| 28 | 32 | Change "below mentioned" to --below-mentioned--. |
| 28 | 52 | Change "1.5024" to --1.5024 g--. |
| 29 | 17 | Change "ybenzyloxycarbonyl L-aspartyl" to --ybenzyloxycarbonyl-L-aspartyl--. |

Signed and Sealed this

Eighteenth Day of June 1985

[SEAL]

Attest:

DONALD J. QUIGG

Attesting Officer

Acting Commissioner of Patents and Trademarks